US008785401B2

(12) United States Patent
Cunningham et al.

(10) Patent No.: US 8,785,401 B2
(45) Date of Patent: *Jul. 22, 2014

(54) METHODS FOR TREATING DISEASES HAVING AN INFLAMMATORY COMPONENT RELATED TO PHOSPHOLIPASE A2

(75) Inventors: Timothy J. Cunningham, Fort Washington, PA (US); Lihua Yao, Wynnewood, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 398 days.

This patent is subject to a terminal disclaimer.

(21) Appl. No.: 11/988,253

(22) PCT Filed: Jul. 10, 2006

(86) PCT No.: PCT/US2006/026568
§ 371 (c)(1),
(2), (4) Date: Jan. 15, 2009

(87) PCT Pub. No.: WO2007/008690
PCT Pub. Date: Jan. 18, 2007

(65) Prior Publication Data
US 2009/0181879 A1    Jul. 16, 2009

Related U.S. Application Data

(60) Provisional application No. 60/697,598, filed on Jul. 8, 2005.

(51) Int. Cl.
*A61K 38/08* (2006.01)
*A61P 29/00* (2006.01)
*C07K 7/06* (2006.01)

(52) U.S. Cl.
USPC .................... 514/21.6; 514/12.2; 530/328

(58) Field of Classification Search
None
See application file for complete search history.

(56) References Cited

U.S. PATENT DOCUMENTS

| | | | |
|---|---|---|---|
| 5,866,318 A | 2/1999 | Rydel et al. | |
| 7,528,112 B2 * | 5/2009 | Cunningham et al. | 514/1.1 |
| 8,106,019 B2 * | 1/2012 | Cunningham et al. | 514/21.7 |
| 2003/0225011 A1 | 12/2003 | David et al. | |
| 2004/0132665 A1 | 7/2004 | Cunningham | |
| 2004/0209307 A1 | 10/2004 | Valkirs et al. | |

FOREIGN PATENT DOCUMENTS

| | | |
|---|---|---|
| WO | WO99/51736 | 10/1999 |
| WO | WO2004/059293 | 7/2004 |

OTHER PUBLICATIONS

Stangel M. Remyelinating and neuroprotective treatments in multiple sclerosis. Exp Opin Investig Drugs, Apr. 2004; 13(4):331-347.*

Abe et al.,1987, J Neurochem 48:503-509.
Abraham et al., 2003, Crit Care Med 31:718-728.
Andreis et al., 1999, Life Sci 64:1287-1294.
Bazan et al., 2002, Prostaglandins Other Lipid Mediat 68-69:197-201.
Bolton et al., 1986, J Neuroimmunol 10(3):201-208.
Bolton et al., 1984, J Neuroimmunol 6(3):151-159.
Brusaferri et al., 2000, J Neurol 247:435-442.
Crowl et al., 1991 J Biol Chem 266:2647-2651.
Cummings et al., 2000, J Pharmacol & Exp Therap 294:793-799.
Cunningham et al., 2004, J Neurotrauma, 21(11):1683-1691.
Cunningham et al., 2002, Exp. Neurology, 177:32-39.
Cunningham et al., 2000, Exp. Neurol. 163:457-468.
Cunningham et al., 1998, J Neurosci 18:7047-7060.
Dore-Duffy et al., 1991, Neurol 41(2(Pt 1)):322-334.
Eagleson et al., 1992, Exp Neurol 116:156-162.
Eagleson et al;, 1990, Exp Neurol 110:284-290.
Flower et al., 1979, Nature 278:456-459.
Gladue et al., 1996, J Exp Med. 183:1893-1898.
Granata et al., 2005, J Immunol. 174:464-474.
Greco et al., 2004, J Neurol Sci 224:23-27.
Hannon et al., 2003, FASEB J. 17:253-255.
Haun et al., 1993, J Neurosci 13(2):614-622.
Kalyvas, 2004, Neuron 41:323-335.
Klivenyi et al., 1998, J Neurochem 71:2634-2637.
Klegeris et al., 2003, J Leukoc Biol 73:369-378.
Klegeris et al., 2000, J Leukoc Biol 67:127-133.
Landgraf et al., 2004, FASEB J. 19(2):225-7.
Lipton, 1999, Physiol. Rev. 79:1431-1568, 1999.
Lukiw et al., 2000, Neurochem Res. 25:1173-1184.
Martino et al. 2002, Lancet Neurol 1:499-509.
Mihelich et al., 1997, Prog Surgery 24:140-145.
Miele L., 2003, J Clin Invest 111:19-21.
Moon et al., 2004, Neurosci Lett 356:123-126.
Neu et al., 1992, Acta Neurol Scand 86:586-587.
Newman et al., 1997, Adv Exp Med Biol 407:249-253.
Peters-Golden et al., 2005, J Immunol 174:589-594.
Pinto et al., 2003, Glia 44:275-282.
Porter et al., 2003, Proc Natl Acad Sci USA 100(19):10931-6.
Reder et al., 1994, J. Neuroimmunol 54:117-127.
Reder et al., 1995 Am J Ther 2:711-720.
Rehncrona et al., 1982, J Neurochem 38:84-93.
Rose et al., 2004, J Neuroimmunol. 149(1-2):40-9.
Saluja et al., 1997, Neurosci Lett 233:97-100.
Sapirstein et al., 2000, Biochimica et Biophysica Acta 1488:139-148.
Schittek et al., 2001, Nat Immunol 2:1133-1137.
Sohn et al., 2003, J Clin Invest 111:121-128.
Springer, 2001, Curr Pharmaceut Design 7:181-198.
Stefferl et al., 2001, Endocrinology 142:3616-3624.
Thommesen et al., 1998, J Immunol 161:3421-3430.
Tilley et al., 2001, J Clin Invest 108:15-23.

(Continued)

*Primary Examiner* — Kimberly A Ballard
(74) *Attorney, Agent, or Firm* — Saul Ewing LLP; Kathryn Doyle

(57) ABSTRACT

The present invention relates to methods useful to monitor central and peripheral nervous system neuron/axon destruction resulting from an increase in acute phase inflammatory enzymes. The methods have applicability to monitoring the progress of neurological diseases, including multiple sclerosis and Alzheimer's disease, as well as neuroinflammatory damage that results from sports injuries, vigorous physical activity or any form of physical abuse. The invention further relates to methods of treating multiple sclerosis or other diseases with an inflammatory component related to phospholipase A2.

2 Claims, 16 Drawing Sheets

(56) References Cited

OTHER PUBLICATIONS

Todorov et al., 1996, Nature 379:739-42.
Valentin et al., 2000, Biochim Biophys Acta 1488:59-70.
Vishwanath et al., 1993, J Clin Invest 92:1974-1980.
Wingerchuk, et al. 2005 Neurology 64(7):390-1.
Yoshida et al., 1986, J Neurochem 47:744-757.
Yoshizawa et al., 1992, J Immunol 148:3110-3116.
Nevalainen 1993, "Serum phospholipases A2 in inflammatory diseases," Clin Chem 39(12):2453-9.
Touqui et al., 2001, "Mammalian secreted phospholipases A2 and their pathophysiological significance in inflammatory diseases." Current Molecular Medicine 1:739-754.
Triggiani et al., "Secretory phospholipases A2 activate selective functions in human eosinophils." 2003, J Immunol 170(6):3279-88.
Triggiani et al., 2005, "Secretory phospholipases A2 in inflammatory and allergic diseases: not just enzymes." J. Allergy Clin Immunol 116(5):1000-1006.

* cited by examiner

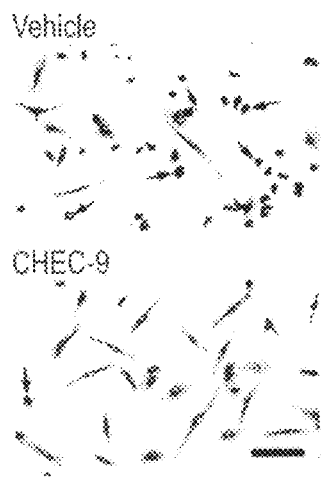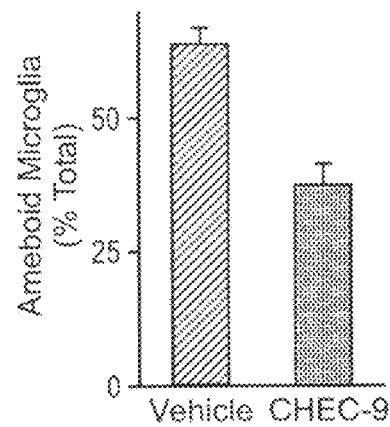
FIG. 5A  FIG. 5B
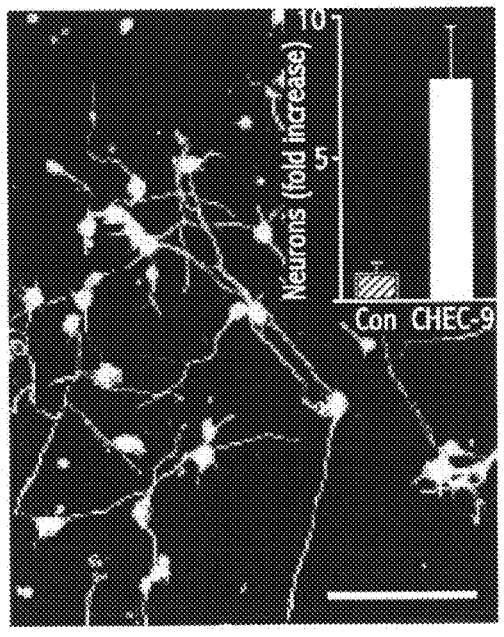
Control  CHEC-9
FIG. 6A  FIG. 6B

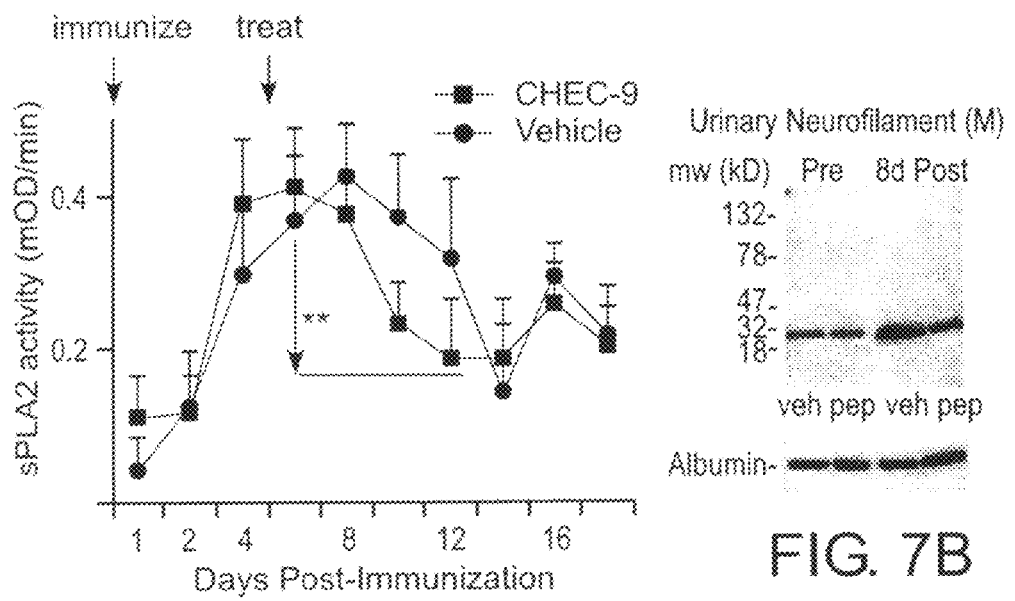
FIG. 7A
FIG. 7B
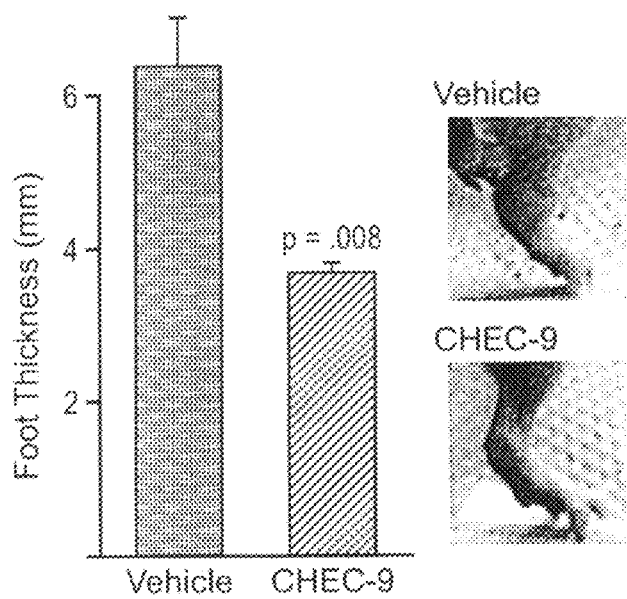
FIG. 8

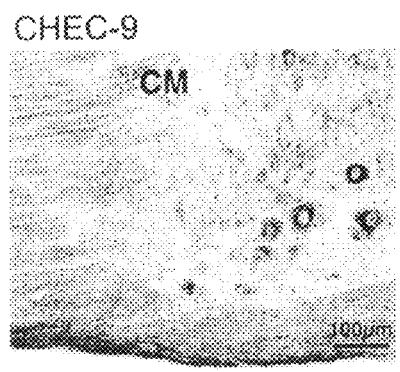
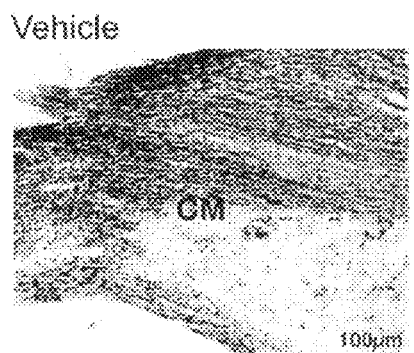
FIG. 11A  FIG. 11B
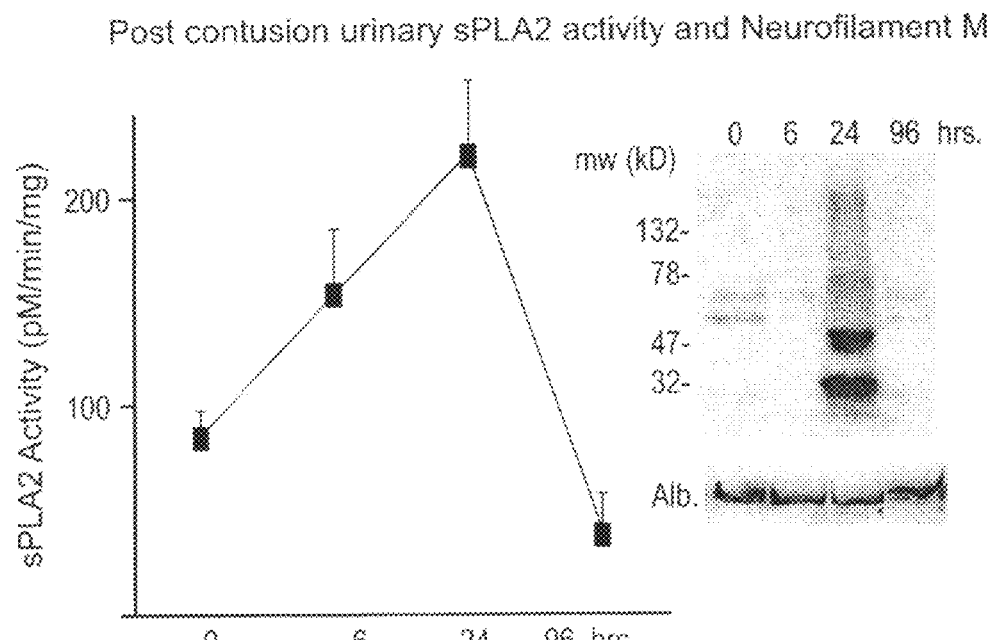
FIG. 12

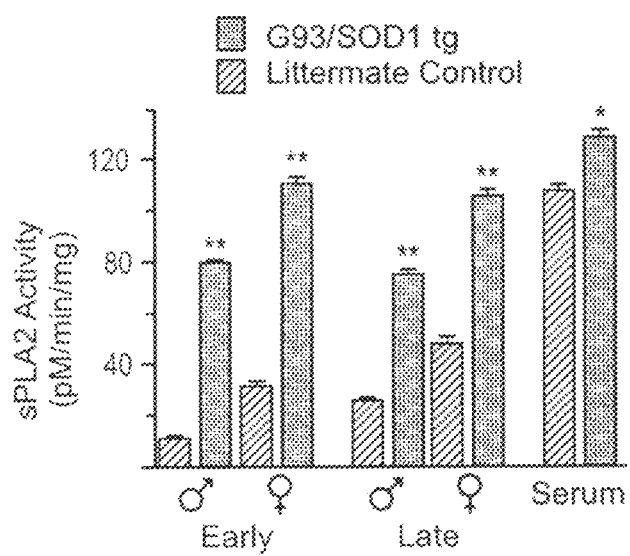 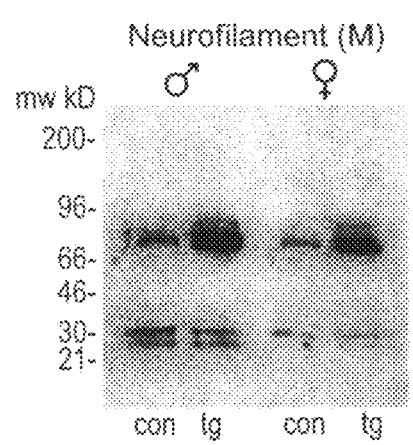
FIG. 14A
FIG. 14B

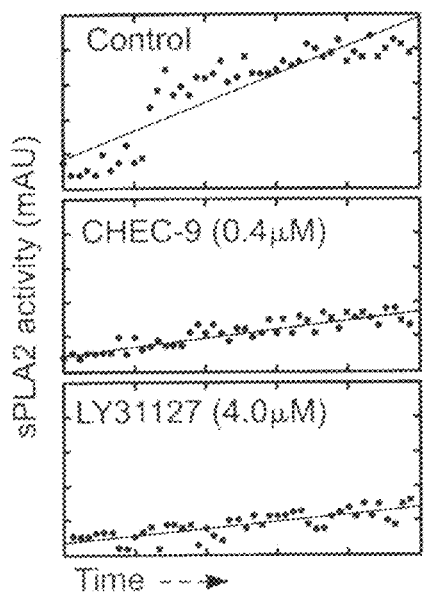
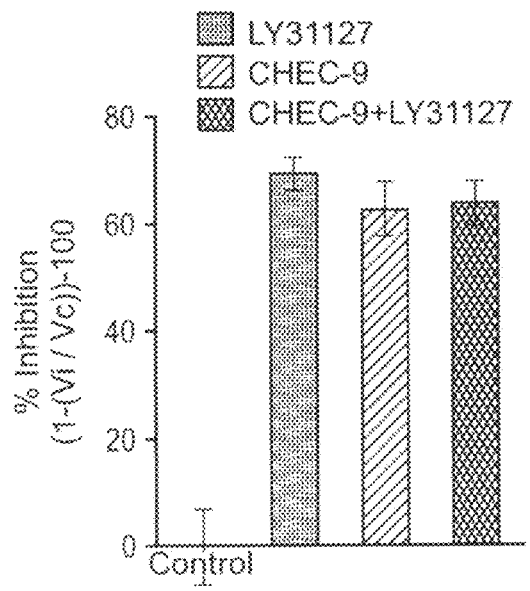
FIG. 19A
FIG. 19B
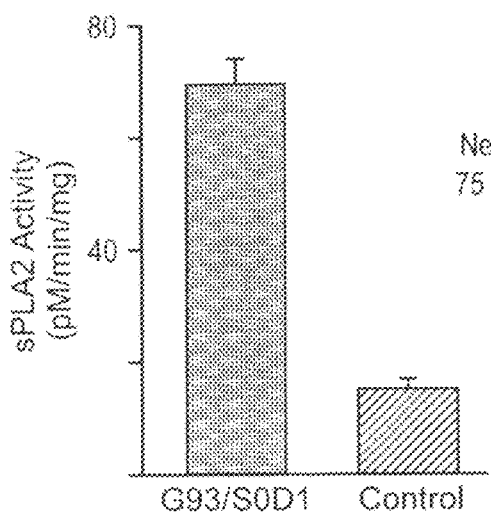
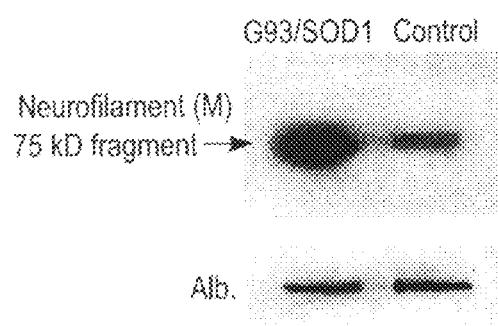
FIG. 20A
FIG. 20B

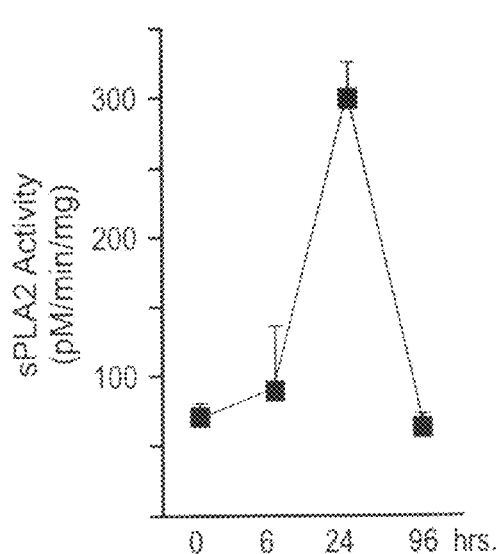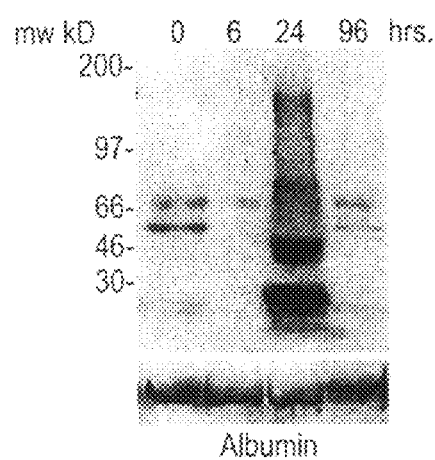
FIG. 21A
FIG. 21B

METHODS FOR TREATING DISEASES HAVING AN INFLAMMATORY COMPONENT RELATED TO PHOSPHOLIPASE A2

This is a National Stage application of PCT International Application No. PCT/US2006/26568, filed Jul. 10, 2006, which in turn claims the benefit pursuant to 35 U.S.C. §119(e) of U.S. Provisional Application No. 60/697,598, filed on Jul. 8, 2005 which is hereby incorporated by reference in its entirety herein.

BACKGROUND OF THE INVENTION

Recent studies with rodent Experimental Autoimmune Encephalitis (EAE) models of Multiple Sclerosis (MS) suggest phospholipase A2 (PLA2) enzymes are involved in the genesis of both the behavioral deficits and the inflammation that characterize this disease (Pinto, et al., 2003; Kalyvas and David, 2004). Systemic sPLA2 enzymes in particular were inhibited in one of these studies by infusion of large molecule sPLA2 substrate decoys. The result was significant behavioral improvement and reduced inflammation.

Multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urological dysfunction, decreased mobility, and depression. Four types classify the clinical patterns of the disease: relapsing-remitting, secondary progressive, primary-progressive and progressive-relapsing (S. L. Hauser and D. E. Goodkin, Multiple Sclerosis and Other Demyelinating Diseases in Harrison's Principles of Internal Medicine 14.sup.th Edition, vol. 2, Mc Graw-Hill, 1998, pp. 2409-2419).

The exact etiology of MS is unknown; however, it is strongly suspected that the demyelination characteristic of the disease is the result of an autoimmune response, perhaps triggered by an environmental insult, e.g. a viral infection. Specifically, it is hypothesized that MS is caused by a T-cell-mediated, autoimmune inflammatory reaction. The autoimmune basis is strongly supported by the fact that antibodies specific to myelin basic protein (MBP) have been found in the serum and cerebrospinal fluid of MS patients, and these antibodies, along with T-cells that are reactive to MBP and other myelin proteolipids, increase with disease activity. Furthermore, at the cellular, level it is speculated that T-cell proliferation and other cellular events, such as activation of B cells and macrophages and secretion of cytokines accompanied by a breakdown of the blood-brain barrier, can cause destruction of myelin and oligodendrocytes. (R. A. Adams, M. V. Victor and A. H. Ropper eds, Principles of Neurology, Mc Graw-Hill, New York, 1997, pp. 903-921). Progressive MS (primary and secondary) may be based on a neurodegenerative process occurring with demyelination.

The pathophysiology of Multiple Sclerosis involves both antigen specific mechanisms and the innate immune system, including several elements of the inflammatory response. MS is not unusual in this regard since inflammation is now recognized as a contributing factor in all disorders in which there is destruction of nervous tissue. Increased hydrolysis of membrane phospholipids by phospholipase A2 is a well-known early response to tissue damage in all organ systems including the nervous system. The activity of these enzymes regulates levels of inflammatory mediators including prostaglandins, leukotrienes, fatty acids, and reactive oxygen species. All these mediators are produced in the early stages of neurodegeneration, regardless of its cause. However, the role of PLA2 activity and many of these downstream PLA2 products has received relatively little attention.

At the present time, there is no cure for MS. Current therapies are aimed at alleviating the symptoms of the disease and arresting its progress, as much as possible. Depending upon the type, drug treatment usually entails the use of disease-modifying agents such as the interferons (interferon beta 1-a, beta 1-b and alpha 2), glatiramer acetate or corticosteroids such as methylprednisolone and prednisone. Also, chemotherapeutic agents, such as methotrexate, azathioprine, cladribine, cyclophosphamide and cyclosporine, have been used. All of the above treatments have side-effect liabilities, little or no effect on fatigue and depression, as well as limited effects on relapse rates and on ability to prevent exacerbation of the disease. Treatment with interferons may also induce the production of neutralizing antibodies, which may ultimately decrease the efficacy of this therapy.

Current and planned disease modifying therapies for MS (in use or in trials) suppress aspects of the acquired immune response. The activities of the two front line treatments, Glatiramer acetate and Interferon beta, are not fully understood, but these operate at least in part by regulation of T cell proliferation and apoptosis. Natalizumab (TSAYBRI, Biogen), a humanized IgG4 antibody that binds to alpha-4 integrins, interferes with transvascular migration of immune reactive cells including T cells. Newer oral compounds, now in trials (e.g., FTY720, Novartis; BG-12, Biogen; Laquinimod, Teva, Mitoxantrone, Wyeth), are also designed to inhibit immune cell proliferation and/or trafficking. The drawbacks of this general approach are increasingly apparent. Either the drug has limited effectiveness or, with increasing efficacy, normal immune surveillance is compromised. For example, the cost effectiveness of Interferon beta is low when measured in terms of Quality Adjusted Life Years (QALY takes into account both EDSS score and longevity). On the other hand, Natalizumab appears to be very effective in limiting relapses, but was withdrawn during clinical trials because of cases of progressive multifocal leukoencephalopathy, a rare but often fatal disease resulting from opportunistic JC virus infections. CHEC-9 is an anti-inflammatory and neuron survival-promoting peptide. In the first instance, it inhibits enzymes that initiate a cascade of changes during the early stages of inflammation, so like other drugs that operate in this pathway (e.g. the COX inhibitors), it may have minimal effects on critical functions of the acquired immune response. On the other hand, it is possible that elimination of the early inflammatory component of MS will limit subsequent events in the cascade such as BBB breakdown, effusion of immune cells, myelin and axonal degeneration, and thereby inhibit active disease. Our data show that PLA2 inhibition limits these events after acute lesions of the nervous system. The same may be true in EAE, as suggested by our results and the results of others. Since CHEC-9 is an uncompetitive inhibitor, we propose it operates "as needed" when enzyme and substrate levels are high. In addition, the direct cell survival-promoting properties of CHEC-9 may further indicate its potential efficacy in MS, especially in light of new models of the disease that highlight the primary importance of cell degeneration (both neuronal and oligodendrocytic).

Recent studies of rodent experimental autoimmune encephalomyelitis (EAE) models of MS suggest PLA2 enzymes are involved in the genesis of both the behavioral deficits and the inflammation that characterize this disease. Pinto, et al. report that systemic infusion of substrate-like molecules, presumably targeting secreted (s)PLA2s, is effective in reducing inflammation and clinical EAE disease. However, the status of MS patients with regard to PLA2 activity is unknown, so it is not clear whether these enzymes are indeed a worthwhile target for MS treatment.

Despite the foregoing developments, there is a need for a method which provides a non-invasive method of discovering and monitoring inflammation and neuron degeneration. Moreover, there still exists a strong need for new treatments to combat the progression and symptoms of MS. The present invention meets these needs.

BRIEF SUMMARY OF THE INVENTION

In an aspect of the invention, the invention includes a method of detecting inflammation in a mammal comprising obtaining a sample of a bodily fluid, detecting in the bodily fluid an increase in the activity of at least one inflammatory enzyme, and detecting at least a fragment of at least one nervous system specific protein. In an aspect, the nervous system specific protein is detected using an antibody-based assay.

In an aspect, the invention includes a method of detecting degeneration of a neuron comprising obtaining a sample of a bodily fluid, detecting an increase in the activity of an inflammatory enzyme, and detecting at least a fragment of at least one nervous system specific protein.

In an aspect of the invention, a method of detecting degeneration of an axon comprises obtaining a sample of a bodily fluid, detecting an increase in the activity of an inflammatory enzyme, and detecting at least a fragment of at least one nervous system specific protein. In an aspect, an inflammatory enzyme is a phospholipase A2 enzyme. In another aspect, the body fluid comprises urine.

In an aspect, the invention includes a kit for detecting inflammation in a mammal, including a first component for detecting the activity of at least one inflammatory enzyme, a second component for detecting at least a fragment of at least one nervous system-specific protein in the sample, an applicator, and an instructional material for the use thereof. In an aspect, the first component comprises at least two separate reagents, further wherein each reagent detects a distinct inflammatory enzyme. In another aspect, a first component comprises a reagent that detects phospholipase A2 activity. In yet another aspect, a first component comprises a reagent that detects phospholipase A2 protein. In still another aspect of the invention, a second component comprises at least two separate reagents, further wherein each reagent detects a distinct nervous system-specific protein or fragment thereof.

In an aspect, the invention includes a kit for detecting degeneration of a neuron in a mammal comprising a first component for detecting the activity of at least one inflammatory enzyme, a second component for detecting at least a fragment of at least one nervous system-specific protein in the sample, an applicator, and an instructional material for the use thereof.

In an aspect of the invention, a kit for detecting degeneration of an axon in a mammal includes a first component for detecting the activity of at least one inflammatory enzyme, a second component for detecting at least a fragment of at least one nervous system-specific protein in the sample, an applicator, and instructional material for the use thereof.

The invention also includes a method of treating a mammal having MS, the method comprising administering a therapeutically effective amount of a polypeptide to a mammal, wherein the polypeptide inhibits the activity of PLA2. In an aspect, the polypeptide is CHEC-9. In another aspect, the polypeptide is administered by at least one route selected from the group consisting of parenterally, orally, intramuscularly, and systemically.

The invention also includes a method of monitoring the progression of MS in a mammal, comprising taking a first measurement of PLA2 activity in a first urine sample obtained from a mammal, taking a second measurement of PLA2 activity in a second urine sample obtained from the mammal, wherein the second sample is obtained at a later time than the first sample, and comparing the first and second measurements, wherein a second measurement larger than the first measurement is an indication that the MS is progressing in the mammal.

The invention also includes a method of treating a mammal afflicted with an inflammatory condition, the method comprising administering a therapeutically effective amount of a polypeptide to a mammal, wherein the polypeptide inhibits the activity of PLA2. In an aspect, the polypeptide is CHEC-9. In another aspect, the polypeptide is administered by at least one route selected from the group consisting of parenterally, orally, intramuscularly, and systemically.

The invention also includes a method of monitoring the progression of an inflammatory condition in a mammal, comprising taking a first measurement of PLA2 activity in a first urine sample obtained from a mammal, taking a second measurement of PLA2 activity in a second urine sample obtained from the mammal, wherein the second sample is obtained at a later time than the first sample, and comparing the first and second measurements, wherein a second measurement larger than the first measurement is an indication that the inflammatory condition is progressing in the mammal.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments, which are presently preferred. It should be understood, however, that the invention is not limited to the precise arrangements and instrumentalities shown. In the drawings:

FIG. 5, comprising FIGS. 5A-5B, illustrates that CHEC-9 inhibits LPS stimulated 'deramification' of microglia in vitro. Purified microglia (95%+ by ED-1 staining) were treated with 25 nM LPS and after 20 min CHEC-9 was added to a final concentration of 10 pM. The cultures were terminated after 48 hrs. Peptide treatment produces a significant reduction in the percentage of ameboid cells (examples are marked by arrows). Vehicle—64±3.0% (n=8) vs. CHEC-9—37±3.8% (n=8) p=3×10$^{-4}$ while the total numbers of microglia in the two conditions is similar (relative to vehicle=100±6%, CHEC-9=99.4±6%). The cells were stained with an antibody to tumor necrosis factor alpha Bar=100 μm. Center panels are fluorescence images from a similar experiment showing most of the TNFα+ cells (green) also stain with ED-1 (red). Areas of overlap=yellow.

FIG. 6, comprising FIGS. 6A-6B, illustrates that CHEC-9 increases survival of purified cortical neurons. The micrographs are of neocortical neurons from 1 day old rats after 4 days in vitro. Cortical neurons were allowed to differentiate for 24 hours on poly-L-lysine at low density (1×10$^4$ cells/cm$^2$) in N2 medium. On day 2, the medium was changed and the cells treated with CHEC-9 or DMEM vehicle. Low density seeding in the near complete absence of astrocytes along with the medium change produce a substantial amount of oxidative stress and cell death in the cultures. CHEC-9 treatment increases the number of surviving neurons by more than 7 fold (CHEC-9—772±186% vs. vehicle—100±32%). Cells are stained with the TUJ1 antibody to neuronal tubulin (isotype III). Bar=100 μm.

FIG. 7 illustrates the time course of changes in urinary sPLA2 activity following bilateral footpad immunization of DA rats with guinea pig myelin basic protein (100 μg total in CFA). Single voids from each rat were collected in metabolic cages between 9 AM and 2 PM on PI days 1 and 2 and every other day after day 2. Significant elevations in activity are found at 4-6 days PI followed by a decline. Treatment with CHEC-9 was between 2-5 PM everyday on PI days 5-15. The pattern of the sPLA2 curves in CHEC-9 and control-treated rats is somewhat similar before and after treatment. However, mean activity after 2 days of treatment was significantly attenuated by CHEC-9 (days 4 & 6 PI vs. 8 & 10 PI, p=0.007, **) but not after vehicle treatment (p=0.528 for the same period). Comparisons between groups within this period was not significant apparently because of variability in the values for individual vehicle-treated rats. Right: Western blots were prepared from pooled urine samples collected before immunization and 8 days after immunization. The urine samples were dialyzed 20 hrs. at 4° against 2 changes of 1000-fold excess of 20 mM tris-HCL, 200 μg protein loaded for immunoblotting of SDS gels (reducing) using a monoclonal antibody to 160 kD neurofilament protein. The blots were stripped and reacted for albumin as a loading control. The NF Ab is not cross reactive with other NF proteins or with intermediate filaments in muscle, and samples are not cross reactive with secondary antibodies. The blots suggest a post-immunization increase in a 30 kD NF (M) fragment that is most prominent in the vehicle-treated rats. A similar fragment is found in other neuropathological conditions and has been suggested to be dependent on endogenous trypsin-like enzymes (Fasani, et al., 2004). The excess in vehicle-treated rats could be the result of increased axon destruction (either central or peripheral) since we find the urinary levels of NF fragments (of different sizes) are also exaggerated in other neurodegeneration models (see below). Their appearance in normal animals could represent normal peripheral axon turnover (review by Gordon, et al., 2004). However, the origin of these fragments is unknown at present.

FIG. 8 illustrates foot edema in CHEC-9 and vehicle treated rats following bilateral foot pad immunization with myelin basic protein/CFA. The thickness of the feet was measured 10 days post immunization. CHEC-9 treatments began 5 days earlier. Measurements were made from planter to superior surface of the foot just rostral to the heel. The difference between the two groups is significant designating either rats (n=5, each condition) or feet (n=10) as the unit of observation (p=0.008, 0.002 respectively).

FIG. 11, comprising FIGS. 11A and 11B, shows micrographs showing the region of the conus medularis (CM) in the spinal cord of two EAE rats treated with CHEC-9 (rat #411) or vehicle (rat #410) and sacrificed 18 days after immunization. The two parasagittal sections represent nearly equivalent medio-lateral planes. There is extensive spinal cord and cellular atrophy (and/or cell infiltration) in rat 410 as well as large areas of myelin degeneration (note scale bars are equal). The clinical EAE score is shown for these two rats and consistent with the histology. Nissl-myelin stain (cyanine R followed by cresyl violet).

FIG. 12 shows sPLA2 activity following contusion of the spinal cord. The lesion was made with the MASCIS impact device set at 25 mm weight drop (see Young, 2002) in 5 rats who were otherwise untreated. Urine samples were collected at the indicated times (0=prior to surgery). Enzyme activity is expressed relative to total protein. Western blots were prepared as described in FIG. 7. Samples=200 µg (Blots were stripped for reaction with albumin Ab as loading control). Maximal sPLA2 activity and maximal excreted NF is found at either 6 (1 rat) or 24 hrs (4 rats) and the two were correlated; shorter survival times were not examined.

FIG. 14, comprising FIGS. 14A and 14B, illustrates an increased sPLA2 activity urine and serum of G93A/SOD1 mutant mice. Twenty-50 µl of urine was collected and each of 12 symptomatic G93/SOD1 mutant mice and 12 littermate controls. The samples were collected at two symptomatic stages 80-85 and 129-134 days and pooled according to the gender of the mice. Whole blood from both sexes was collected at the later ages and serum samples were prepared by centrifugation. The urine was dialyzed against 2 changes of 1000 fold excess of 20 mM tris-HCL, total protein determined, and secreted phospholipase A2 (sPLA2) activity measured in 3-4 samples from each pool. The results were highly significant (no overlap between the values obtained from tg and control mice for any comparison, corrected for multiple comparisons). Western blots were also prepared from the later samples after loading 12.5 µg total protein on SDS gels and immunostaining with a polyclonal rabbit antibody to medium neurofilament protein with minimal cross reactivity with other NF proteins. A prominent 75 kD appears in urine which may represent a calpain dependent proteolytic fragment of NF(M) (Stys and Jiang, 2002). Loading controls (not shown) and other reactive bands on the gel indicate that total protein concentration as measured and loading were equivalent. The origin of urinary neurofilament is unknown although possibly from axon turnover in PNS of control mice (see FIG. 7). Excess in symptomatic mutant mice could represent additional protein from degenerated spinal neurons and axons (both CNS and PNS). Accumulation of neurofilaments in diseased neurons of ALS patients is well known (review by Rao and Nixon, 2003). SPLA2 activity and NF levels are unrelated to total urinary protein (one estimate of kidney function). Additional controls, e.g., creatine kinase measurements, application of PNS and CNS specific markers, are in progress.

FIG. 19, comprising FIGS. 19A and 19B, are graphs demonstrating that both CHEC-9 and Lilly sPLA2 II inhibitor (LY311727) reduce human plasma sPLA2 activity by 60-70% with non additive effect. Both inhibitors may target the same sPLA2 enzyme pools.

FIG. 20, comprising FIGS. 20A and 20B, shows a graph and a picture of a gel demonstrating sPLA2 activity in progressive disease in an ALS model. Ongoing increases are found in both serum and urine of symptomatic G93/SOD1 transgenic mice. The graph shows urinary sPLA2 activity. The same urine samples have large increases in a fragment of NF (M) which may reflect neuron/axon destruction.

FIG. 21, comprising FIGS. 21A and 21B, shows a graph and a picture of a gel demonstrating monitoring acute sPLA2 activity in spinal cord contusion. The graph shows sPLA2 activity at 4 points following spinal contusion in rats and corresponding increases of NF fragments in urine samples. Urine is more suitable than serum for monitoring levels of neuron specific proteins because of lower concentration of interfering proteins.

FIG. 22, comprising FIG. 22A illustrates velocities of PLA2 enzyme reactions at different substrate concentrations [S] are shown for 25 µl sample of urine from a 37 y.o. patient with stable MS, compared to an age/gender matched control. Typical hyperbolic curves were obtained for urine samples from both patients and controls, i.e., reaction velocity peaks and levels off at high [S]. Velocity is therefore proportional to the concentration of active enzyme in the urine at saturating substrate concentrations (Michaelis-Menton equation, $Vmax=K_2[E]$). Mean and s.e.m. of triplicate reactions for each concentration are shown. Inset: Western blot of 200 µg total urinary protein of 34 y.o. patient with active MS. A 14 kD sPLA2 immunoreactive band appeared (arrow) along with a 68 kD immunoreactive band of unknown identity. FIG. 22B illustrates the level of enzyme activity in MS patients with active or stable disease compared to controls, as described elsewhere herein. All measurements were made using 600 µM substrate and normalized to the average control value. There was a significant 4 and 6-fold increase in PLA2 activity compared to controls in the stable and active MS patients respectively, (p=0.049*; 0.0019**, for comparison with controls).

FIG. 23, comprising FIG. 23A depicts that PLA2 enzymatic activity, normalized to pre-immunization values, increased steadily to day 8 in both CHEC-9 and vehicle-treated rats. A significant reduction in activity was observed on days 10 and 12 post-immunization in the peptide treated group either by comparing values of peptide and vehicle directly (p=0.049, 0.026 respectively), or by peak to trough comparison between days 8 and 12, where reduction in sPLA2 levels with peptide treatment was significant (p=$10^{-3}$) but in vehicle-treated rats was not (p=0.491). FIG. 23B depicts that mean clinical scores from day 10 onwards were also significantly lower in the peptide treated rats (p<$10^{-4}$).

DETAILED DESCRIPTION OF THE INVENTION

Figure 1:
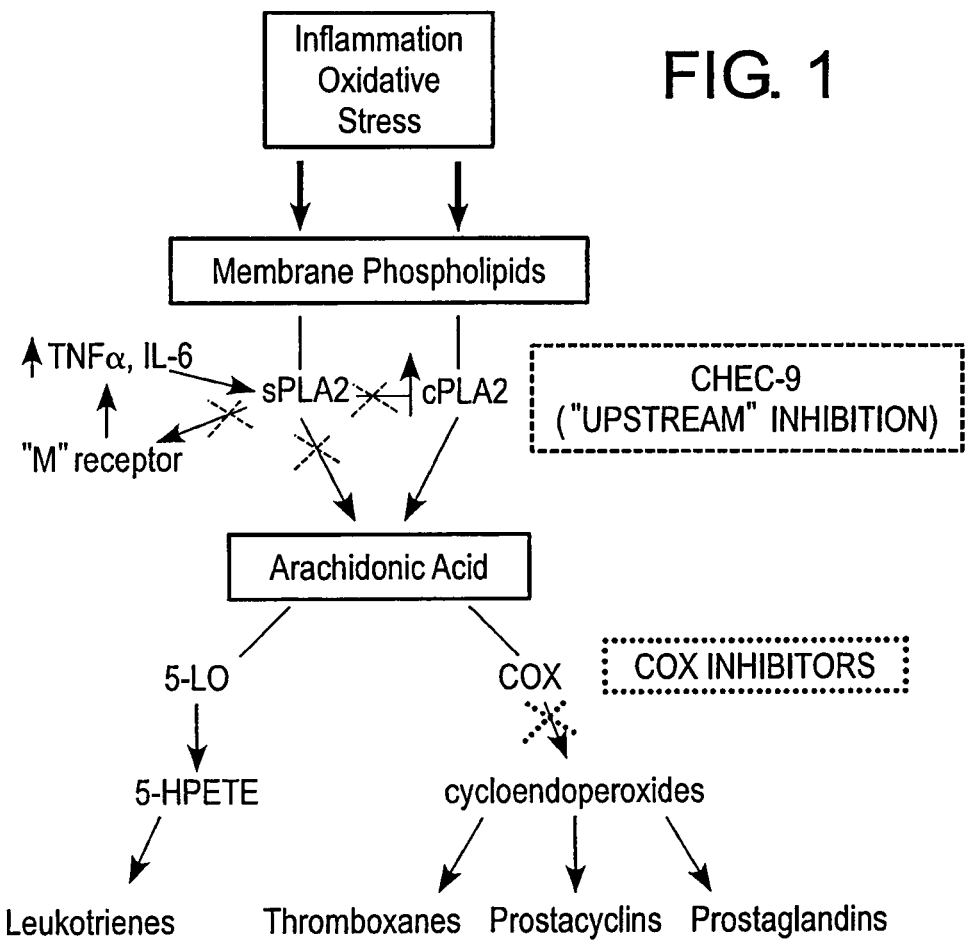
FIG. 1 is a diagram of PLA2-pathways involved in production of inflammatory mediators. Inflammation and oxidative stress result in increased production of Arachidonic Acid (AA) from membrane phospholipids and of several classes of AA derived inflammatory mediators (bottom of the figure). Under these conditions sPLA2 contributes directly and indirectly (via cPLA2) to AA production and therefore to both lipoxygenase (5-LO) and cyclooxygenase (COX) branches of the AA pathway producing these mediators. SPLA2 also contributes to increased levels of proinflammatory cytokines via several cellular pathways including sPLA2 "M" receptors. CHEC-9 (SEQ ID NO:1) may inhibit many of these pathways "upstream" as compared to (for example) COX inhibitors which are restricted to the downstream cyclooxygenase derived mediators. Levels of representative AA derivatives and related cytokines will be determined in serum and spinal cord of the proposed models of CHEC-9 therapy for MS.
Figure 2:
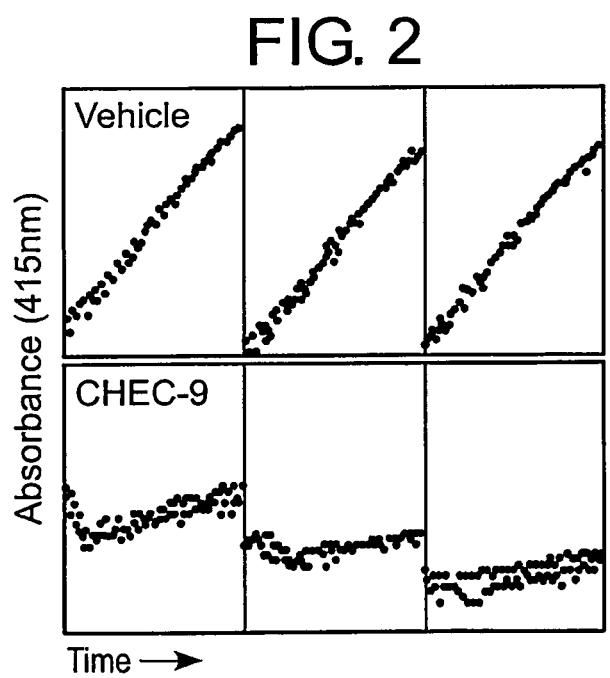
FIG. 2 illustrates sPLA2 activity of 8% plasma samples prepared from whole blood of healthy 57 year old male. Whole blood was incubated with 400 nM CHEC-9 (final concentration) for 2 hrs. at 4° and then samples were used to hydrolyze an sPLA2 specific substrate to give a product detected at 415 nm absorbance. The reaction was inhibited upon CHEC-9 treatment. Three enzyme reactions are shown and data is representative of that obtained from all 4 healthy volunteers. These curves, along with velocity of the reaction (Absorbance/time or milliOD/min), and several other reaction parameters are calculated by software supporting the kinetic reader. The substrate, buffer and other details of the assay are described elsewhere herein.

The present invention includes the identification, detection and/or monitoring of inflammation, via secreted phospholipase A2 enzyme activity. The invention also includes the identification, detection and/or monitoring of neuron degeneration via monitoring of levels of nervous system-specific proteins using techniques including, but not limited to, Western blotting, ELISA or a multiplex assay using urine or other bodily fluids. The invention is applicable to a variety of disorders (e.g., emotional or physical stress, all neurodegenerative disorders, injuries due to prize fighting). The method is based, in part, on the discovery that active sPLA2 enzyme and fragments of nervous system specific proteins are excreted, and in the case of animal models of neurodegenerative diseases (like MS and ALS), and they are secreted at the time of or before symptoms.

The invention further includes methods of treating MS and other inflammation-associated diseases or disorders. In particular, the invention includes methods of treating MS and other inflammation-associated diseases or disorders which are associated with PLA2 activity. This is because it has been shown herein that a polypeptide, CHEC-9, can inhibit the activity of PLA2.

Definitions

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, and the like, for administering CHEC-9 or other inhibitor of the invention to a mammal.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

A "therapeutically effective amount" of a compound is that amount of compound which is sufficient to provide a beneficial effect to the subject to which the compound is administered. By way of a non-limiting example, a therapeutically effective amount of CHEC-9, for the purpose of treating MS, is an amount of CHEC-9 which is sufficient to alleviate one or more symptoms in a patient, the symptoms being associated with MS in the patient.

As used herein, the term "alleviate" refers to the lessening, decrease, or diminishing of a symptom, state, or condition. In one aspect, a symptom of a disease is alleviated when the symptom decreases in severity of occurrence or effect in a patient. In another aspect, a symptom of a disease is alleviated when the symptom is completely eradicated or eliminated from the patient.

As used herein, the term "treat" or "treating" refers to alleviating one or more symptoms of a disease or disorder in a mammal.

As used herein, the term "degeneration of a neuron" refers to any decrease in activity, viability, or function of a neuron from the normal healthy state of the neuron. In one aspect, degeneration of a neuron refers to a minor decrease in activity, viability, or function of a neuron from the normal healthy state of the neuron. In another aspect, degeneration of a neuron refers to the complete incapacitation of the neuron such that the neuron cannot function in any capacity, and even death of the neuron. The term "degeneration of axon" similarly refers to the activity, viability or function of an axon.

As used herein, the term "detecting an increase" of a protein, compound or activity refers to the measurement of a level of protein, compound or activity, wherein the measurement reflects a value higher than the value obtained from an identical measurement under a healthy, non-diseased condition in a subject. By way of a non-limiting example, a measurable increase in the activity of PLA2 in the urine of a subject with MS is one way to "detect an increase" in PLA2 activity, wherein the increase is compared to the level of PLA2 activity in the urine of the subject without MS. The skilled artisan will understand that the level of activity of PLA2 in the urine of a subject having MS, for example, can be standardized against the level of PLA2 activity in a separate, healthy patient, in order to "detect an increase" in the urine PLA2 activity in the patient afflicted with MS.

As used herein, the term "at least a fragment" refers to a polypeptide comprising at least two consecutive amino acid residues, wherein the consecutive amino acid residues correspond to the sequence of a larger peptide or protein. By way of a non-limiting example, the dipeptide Ser-Arg is a fragment of a larger polypeptide containing the sequence Ser-Arg within the overall polypeptide. Similarly, the dipeptide Ser-Arg is a fragment of a larger polypeptide consisting of the sequence Ser-Arg-Gly. That is, a polypeptide lacking even one amino acid residue is "at least a fragment" of the larger, complete polypeptide.

In recent years, there has been a renewed interest in the axonal injury and cell death that occurs in MS and a "shift in focus" in MS research from antigen-specific mechanisms to the role of the innate immune system in neurodegeneration (reviews by Bjartmar and Trapp, 2001, Hendriks, et al., 2005; Prat and Antel, 2005). The reason for this shift is the recognition that tissue damage (axonal loss) begins at disease onset and sets up a neuroinflammatory cascade that leads to progressive disability often found in long term MS patients. Phospholipase A2-directed inflammation has long been recognized as an early response to tissue damage in all organ systems including the nervous system (Cummings, et al. 2000; Bazan, et al. 2002). The activity of these enzymes regulates levels of inflammatory mediators including prostaglandins, leukotrienes, fatty acids, and reactive oxygen species (ROS). All these mediators are produced in the early stages of neurodegeneration, regardless of etiology. However the role of PLA2 activity and many of these downstream mediators in the destruction of nervous tissue, especially in MS, has received relatively little attention compared to neurotransmitter related molecules or proinflammatory cytokines, both of which may be regulated by PLA2 activity. As noted by Lipton (1999), the understanding of the contribution of PLA2 directed activities to neurodegeneration is limited by the lack of useful inhibitors. In fact, most of the small molecule (non-peptide) inhibitors that have been developed commercially (generally targeted to secreted or sPLA2s) have not been successfully applied to in vivo paradigms in any organ system, let alone the nervous system (review by Springer, 2001, see also below). Peptides that are PLA2/transglutaminase inhibitors have recently been identified, but so far these have been applied only as topical agents in a conjunctivitis model (Miehle, et al. 2003; Sohn, et al., 2003). Furthermore, up until recent studies of rodent EAE and experiments with CHEC-9 applied to CNS trauma (Cunningham, et al. 2004), there were no reports that directly linked endogenous sPLA2 activity to neurodegenerative events in vivo. These recent studies suggest that the sPLA2 contribution is in fact substantial. Since CHEC-9 may also be an effective treatment for EAE, the present invention provides a way to target this enzyme in MS models and the blood of MS patients as a further utilize this peptide's clinical potential.

Phospholipases designated A2 (PLA2) make up a large family of related enzymes that have been classified into groups I-XII according to sequence homology, cellular localization and associated biological activities (reviews by Fuentes, et al., 2002; Taketo and Sonoshita, 2002; Chakraborti, 2003). PLA2 enzymes are responsible for the hydrolysis of the 2-acyl bond of 3-n-phosphoglycerides. (These enzymes are named A2 to denote their 2-acyl specificity.) Over 25 isoforms have been identified and are organized in three general categories as secreted, cytosolic, or calcium-independent. Group I, II, V, and X PLA2 are closely related enzymes with molecular masses of 13-20 kDa, and are collectively known as the secreted phospholipases (sPLA2). These are further characterized by several disulphide bonds and are a requirement for millimolar amounts of $Ca^{2+}$ for catalytic activity. The sPLA2 enzymes all have a common mechanism involving a catalytic histidine.

PLA2 enzymes are responsible for the first step in arachidonic acid (AA) metabolism, producing AA for processing by cyclooxygenase (COX) and lipoxygenase (LOX) enzymes into prostanoids and leukotrienes (eicosanoids, FIG. 1). Manipulation of one of downstream participants in these pathways, the COX enzymes, has become a focus of reparative neuroscience since these enzymes may make a significant contribution to the inflammatory component of many acute and chronic neurodegenerative disorders, (reviews by Lukiw and Bazan 2000; Bazan, et al, 2002). The contribution of PLA2 activity (i.e., upstream activity), especially that of sPLA2, has received considerably less attention even though these enzymes have long been associated with well known inflammatory conditions outside the nervous system (summarized by Trigianni, et al., 2003). Increased levels of extracellular sPLA2s have been detected in the plasma of patients affected by systemic inflammatory diseases such as acute pancreatitis, septic shock, extensive burns, and autoimmune diseases. sPLA2s accumulate in inflammatory fluids such as the synovial fluid of patients with rheumatoid arthritis, the bronchioalveolar lavage of patients with bronchial asthma, and the nasal secretions of patients with allergic rhinitis. Several groups have shown that sPLA2s are released at sites of allergic reactions, such as the airways of patients with bronchial asthma and the nasal mucosa of patients with allergic rhinitis.

As demonstrated elsewhere herein, sPLA2 enzyme activities make significant contributions to the inflammation and neurodegeneration found in MS. Indeed, there is now widespread appreciation of many of the extracellular and intracellular chemical pathways related to PLA2s involvement in the inflammatory response, however, these pathways are complex and many of the details (as well as general organizing principals) are unknown. It is nonetheless certain that an inflammatory stimulus produces a profound and rapid response in the PLA2-AA pathway of most cell types and that there are amplification mechanisms in place involving: 1) interactions between secreted (s) and cytosolic (c)PLA2s; and 2) cross talk between PLA2 enzymes and cytokines and other inflammatory mediators. In the first instance, it is now clear that sPLA2s and cPLA2s collaborate in the production of and release of AA in a number of cell types (Mounier, et al 2004; Han, et al 2003; Fonteh, 2000; Balboa et al, 2003; Murakami, et al 2002; Hernandez, 1998). It is shown that sPLA2 involvement in AA release occurs during secretion of the enzyme from cells and is amplified if cells are subjected to oxidative stress (as during an inflammatory event). The process can also be driven by autocrine loops. For example, production of sPLA2 IIa (probably the most abundant circulating PLA2 isoform) may be regulated by peroxisome proliferator-activated receptor α (PPARα), a receptor for several AA products (eicosanoids), and its response element PPRE-1, because the latter drives expression of the IIa enzyme. There are numerous opportunities for cross talk between proinflammatory cytokines and components of the PLA2-AA pathway. The relationship between acute phase cytokine mediators and sPLA2 has been recognized for several years (Crowl, et al., 1991 Valetin and Lambeau, 2000; Granata, et al., 2005). IL-6 and sPLA2 for example appear to be coregulatory. On one hand, IL-6 may control sPLA2 production from liver and thus regulate systemic sPLA2 levels during the acute phase response. At the same time, noncatalytic sPLA2 enzymes (at least isotypes IB, X and IIA) may drive IL-6 and TNFα production via the "M" type sPLA2 receptor. TNFα activation of NFKappaB is also shown to depend on sPLA2 enzyme activity since this activation is strongly reduced (in keratinocytes) in the presence of specific sPLA2 enzyme inhibitors (Thommesen, 1998). Thus there are several examples of cytokine mediated inflammatory mechanisms directed by the sPLA2 enzymes themselves. Farther downstream, arachidonic acid products (like prostaglandin E2) also contribute to the cascade, again by upregulation of inflammatory cytokines and mediators (e.g., TNFα, iNOS) following activation of NF kappaB (Poligone and Baldwin, 2001). TNFα induced generation of reactive oxygen species may also depend on downstream components of the leukotriene branch of AA pathways (Woo, et al, 2000).

There are also several instances of cross talk in the reverse direction, i.e., from cytokine to pLA2 product or associated enzyme. For example, in smooth muscle cells, SPLA2 (IIa) transcription is regulated by IL1β, in a pathway also involving NFkappaB along with PPARγ (Couturier, at al., 1999). In neuroblastoma, IL-1β upregulates COX-2 and PGE(2) again via an NF KappaB mediated mechanism (Hoozemanns, et al, 2003). PLA2 amplification and cytokine cross talk processes within cells may be interdependent in a process triggered by diffusible sPLA2 enzymes. In rat mesangial cells for example, a variety of sPLA2s are shown to enhance the TNFα-induced sPLA2-IIa expression at the mRNA and protein levels (Beck, et al. 2003).

It is clear from the disclosure herein that sPLA2 enzyme activity regulates several ecosanoids and related cytokines as part of the overall inflammatory response. Cytokine levels and activity in MS have been studied extensively and the contribution of this class of mediators to the disease is both complex and controversial (review by Martino, et al., 2002). Ecosanoids on the other hand, (chiefly, PGE2 and LTB4), are consistently found to be elevated in the CSF of MS patients (Martino, et al., 2002; Greco, et al., 1999; Dore-Duffy, et al. 1991; Neu, et al., 1992; Bolton, et al., 1984). Cyclooxygenase derived mediators have also been measured in animal models. For example, TBXA2 and PGE2 are both increased in spinal cord during active induction phase of the disease and during relapse in a guinea pig allergic encephalitis (Bolton, et al., 1986). These levels correlated with the number of spinal cord lesions. However, the role COX enzymes in the pathogenesis of EAE and MS remains unclear. Indeed, there are reports of amelioration of EAE with COX inhibitors (aspirin and indomethacin, Moon, et al., 2004; Reder, et al., 1994; 1995), although the results are difficult to interpret since they may relate to COX influence on glutamate excitotoxicity rather than enzyme's direct participation in the inflammatory cascade (see also Rose, et al., 2004). It appears that the only systematic investigation of any COX inhibitor in MS patients concerned the fatigue experienced in MS for which aspirin was effective (Wingerchuk, et al. 2005). The proinflammatory leukotrienes have been largely overlooked as inflammatory mediators in and outside the nervous system (Peters-Golden, et al., 2005). There are numerous lipoxygenase inhibitors available commercially, and some of these inhibitors block EAE (Reder, et al., 1995). However this line of investigation has not been pursued nor is it clear whether any lipopxygenase inhibitors are presently candidates for therapeutic development. Specific LTB4 inhibitors (CP-105, 696 developed by Pfizer) ameliorate EAE and eosinophil migration into spinal cord during EAE (Gladue, et al., 1996), although since this original report no further work with these two compounds has appeared.

The increased emphasis on the role of the innate immune response in MS has renewed interest in the participation of monocytes and monocyte derivatives (macrophages/microglia) in the disease (reviews by Raivich and Banati, 2004 Hendriks, et al., 2005; see also Heppner, et al. 2005). The importance of these cells may also be relevant to the contributions of ecosanoids and sPLA2 activity to MS. As expected, AA metabolic pathways are stimulated in activated monocytes (macrophages and microglia). In the COX branch of AA metabolism, monocytes primarily produce PGE2 and TBXA2, and also produce lipoxygenase derivatives (Tilley, et al., 2001). The fact that activation of these AA pathways is toxic to neural cells has been most convincingly demonstrated with microglial cells because inhibitors of the three enzymes—PLA2s (including sPLA2), lipoxygenase, and COX—each reduce neural cell killing activity of microglia in vitro. (Klegeris and McGeer, 2000; 2003). Furthermore CHEC-9, and a 30 mer containing CHEC-9 called Y-P30, and the parent protein for both these called DSEP (see below), have all been found to inhibit the differentiation and/or killing activity of microglia and of activated macrophages, in vivo and in vitro, including activated human HL-60 cells in xenocultures with mouse neural cells (Cunningham, et al., 2002). For CHEC-9 at least, this inhibition may be directly related to sPLA2 inhibition and subsequent inhibition of the production of downstream ecosanoids in the activated cells. Therefore, one reason inhibition of sPLA2 activity is an effective treatment for EAE, and perhaps for MS, may be related to inhibition of the innate immune system's contribution to these diseases, in particular the ecosanoid production in monocytes and their derivatives.

It has been known for at least two decades that fatty acids, phospholipids and other lipid mediators of inflammation are released following brain damage as a result of phospholipase A2 activity (for example, Rehncrona, et al, 1982; Yoshida, et al, 1986; Abe, et al, 1987; Saluja, at al, 1997). These lipid products, along with the coordinated activity of cytokines and other mediators are expected to contribute significantly to the cell death in the nervous system, either that which is observed after acute lesions to the CNS, or that which is found in many progressive neurodegenerative diseases (reviews by Lukiw and Bazan 2000; Bazan, et al, 2002). Furthermore, breakdown of phospholipids could, in general, produce major changes in membrane and myelin function, as well as free radical formation and deficits in signaling due to increases in free fatty acid. All these changes are potentially damaging to most cell types including neurons (Lipton, 1999).

In the present invention, CHEC-9 inhibition of sPLA2 activity correlates with increased survival of cortical neurons in vitro and after cortical lesions. Of the secreted phospholipases, groups Ib, IIa, and III, all have been shown to induce or potentiate neuron death in vitro, sometimes through effects of arachidonic acid on NMDA and/or calcium channels (Yagami, et al, 2003; 2002a; 2002b; DeCoster, et al., 2002; Kolko, et al., 2002). In fact, PLA2 inhibitors directed at all three classes of PLA2 enzymes (secretory, calcium-independent, and cytosolic) reduce glutamate and aspartate release when applied topically to the rat cerebral cortex (Phillis and O'Regan, 1996). In neurodegenerative disorders like Alzheimer's disease, direct involvement of PLA2 in amyloid neuropathy has been suggested as amyloid beta peptides also activate sPLA2 (Lehtonen, et al, 1996). Cytosolic PLA2 (cPLA2), which may be regulated by sPLA2s, especially under conditions of stress (see above), appears to be involved in both acute and chronic disorders involving neuron death. In addition, cPLA2 knockout mice have smaller infarct sizes following MCA occlusion (Sapirstein and Boventre, 2000), and are resistant to dopamine depletion in a Parkinson's disease model (MPTP neurotoxicity, Kilvenyi, et al, 1998).

Corticosteroids act in part by stimulating the endogenous PLA2 inhibitor lipocortin (Annexin 1, Flower and Blackwell, 1979). The target of Annexin 1 is likely cPLA2 (Hannon, et al. 2003; Vishwanath. Et al. 1993; Newman, et al, 1997). Both sPLA2 and cPLA2 recently have been implicated in rodent EAE. However, the experiments suggesting cytosolic PLA2 involvement in this disease (Kalyvas and David, 2004), while probably correct in principle, must be interpreted with some caution. One side effect of AACOF3, (the trifluomethylketone analog of arachidonic acid used to inhibit cPLA2 in the EAE mice of this study), is a several fold increase in the basal release of the entire spectrum of adrenocortical steroids from adrenal cells (Andreis, et al., 1999). This response could explain the resistance of the mice to EAE (Stefferl, et al., 2001). Exogenous steroid treatment does not prevent active disease in MS but does appear to be effective in accelerating short-term recovery in patients experiencing relapse (Brusaferri and Candelise, 2000).

Circulating sPLA2 has been recognized for several years as a possible therapeutic target for inflammatory disorders outside the nervous system, although when last reviewed (Springer, 2001), it appeared that most efforts aimed at the development of small molecule inhibitors of sPLA2 (non-peptide, designed on the basis of active site structure) had been abandoned by commercial interests. One reason for this loss of interest (as suggested by Springer) is the lack of effectiveness of these compounds in in vivo assays. Although two SPLA2 group IIA inhibitors from Eli Lilly have survived, they have not faired well in initial clinical tests involving patients with arthritis and sepsis (Bradley, et al., 2005; Abraham, et al., 2003). There are no reports suggesting that these or other commercially developed sPLA2 inhibitors have been tested in MS models or in models of any nervous system disorder.

DSEP (Diffusible Survival Evasion Polypeptide) (SEQ ID NO:2) was originally identified by treating neural cell lines with hydrogen peroxide. A 30 amino acid survival-promoting N-terminal fragment of DSEP called Y-P30 was purified from the culture medium of these cells by chromatographic and electrophoretic separation techniques (Cunningham, et al, 1998). The peptide promoted the survival of neural cell lines in vitro and of cortical neurons after cerebral cortex lesions (Cunningham, et al 1998; Cunningham, et al 2000). The novel cDNA encoding DSEP and its genomic location have been identified (Cunningham, et al., 2002). The human DSEP gene located on chromosome 12 region q, has 5 exons and 4 introns, and encodes a 12 kD secreted polypeptide. Y-P30 comprises the N-terminus of the secreted molecule. The harsh treatment of the cells prior to peptide purification, as well as the assay and purification steps that followed, were all based on observations made during studies of the "neurotrophic" properties of CNS transplants, and the survival-promoting activity of medium (CM) conditioned both by embryonic cells and cell lines (e.g. Eagleson, et al, 1990, 1992; Haun and Cunningham, 1993). It was clear from these studies that "trophic" activity in vivo was often most apparent when the CM came from cells subjected to oxidative stress, and this observation eventually led to the production of medium enriched with the peptide. This peptide or a very similar molecule was also partially purified from murine adenocarcinoma cells (Todorov, et al, 1996), group Aβ hemolytic streptococci (Yoshizawa, et al, 1992), and from human sweat (Schittek, et al 2001). Most recently, the survival-promoting properties of DSEP and DSEP-derived peptides have been confirmed independently by two separate laboratories (Porter, et al, 2003; Landgraf, et al, 2004).

A variety of in vitro and in vivo models have been used to demonstrate the cell survival-promoting activity and diminished immune cell activity found with this peptide (Cunningham, et al, 1998, 2000, 2002, 2004). DSEP and DSEP peptides promote the survival of neuroblastoma cells, a hippocampal cell line, and primary cortical neurons all subjected to various kinds of stress in vitro. Application of DSEP peptides after cortical lesions protects cortical neurons that would usually degenerate and inhibits the cellular inflammatory response. The peptide is unusual because it can be applied after the perturbation in vitro or after the lesion in vivo, including via systemic administration. Overexpression of DSEP in neural cells results in a phenotype that is similar to that found after Y-P30/CHEC-9 treatment; i.e., resistance to various stressors including monocyte attack (in vitro in xenocultures, and in vivo as xenografts). Furthermore, DSEP may be part of a normal defense mechanism against stress, immune and otherwise, because rats immunized against the human N-terminal peptide have exaggerated cortical lesions as well as increased killing activity in their sera. This killing activity is consistent with increased sPLA2 activity in the immunized rat's serum but that has to be proved. Finally, Y-P30 has been tested in a model of ischemia/anoxia of the cerebral cortex where it rescues MAP2 immunopositive dendrities in cortical area 2, an effect similar to that reported previously after direct suction of lesions at the area 2/3 border (Cunningham, et al. 1998).

The most remarkable properties of DSEP or DSEP peptides found so far are with the nonapeptide CHEC-9. CHEC-9 was discovered because of a serendipitous substitution of a cys for a lys at position 23 of Y-P30 allowing for disulfide stabilization of a nine amino acid loop in the peptide (Cunningham, et al., 2004). CHEC-9 is a potent survival molecule in vivo: a single subcutaneous injection of CHEC-9 (0.4 mg/kg) following a cerebral cortex lesion results in dramatic effects on both the cytoarchitecture around the wound (which is essentially preserved) and on the invasion and differentiation of inflammatory cells, including microglia and macrophages, at the lesion site (which is inhibited). CHEC-9 also increases the survival of purified cerebral cortex neurons and inhibits the morphological differentiation of activated microglia, when added to cultures of these cells at concentrations of 0.1 mM.

CHEC-9 inhibits the activity of a secreted PLA2 group III (from bee venom) in vitro and sPLA2 activity of rat serum. The specific sPLA2 target of CHEC-9 is unknown although rat serum is dominated by sPLA2 type II (Michelich, 1997). Importantly, the sPLA2 inhibitory effects of CHEC-9 can be demonstrated in serum recovered from rats after systemic delivery of the peptide using the same subcutaneous injection that was used to demonstrate the survival and immunomodulatory effects of the peptide after lesions. Phorbol myristate acetate stimulated platelet aggregation, which can be regulated by both secreted and cytosolic phospholipase A2 (see Cunningham, et al., 2004), is also inhibited by CHEC-9. This inhibition is found in vitro after direct treatment of isolated platelets (100 pM CHEC-9) or in platelets isolated from peptide injected rats after subcutaneous delivery of the peptide at neuroprotective concentrations. Most recently we found that CHEC-9 prevents DA rats from developing EAE after immunization with myelin basic protein.

Figures 18A, 18B:
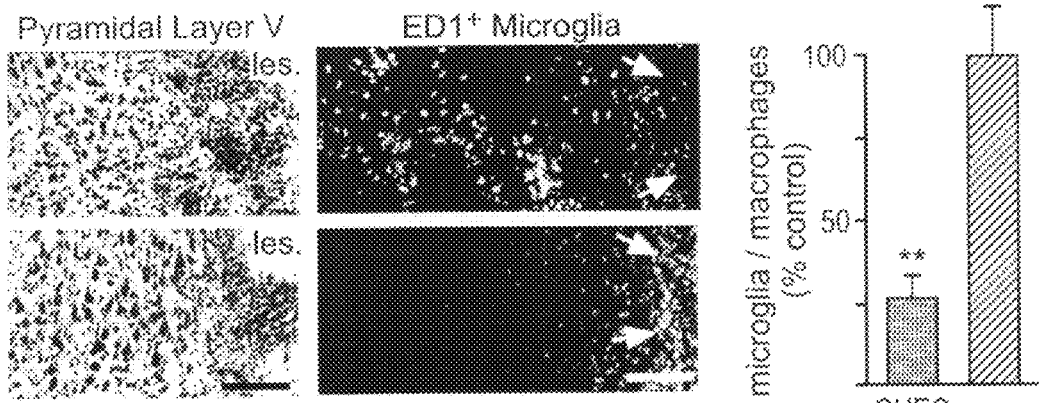
FIG. 18 shows photographs and a graph depicting a control treated (top pictures) and a CHEC-9 treated (bottom pictures) demonstrating that a single subcutaneous injection of peptide CHEASAAQC (CHEC-9) (SEQ ID NO: 1) (0.4 mg/kg) inhibits inflammation and neuron death after cerebral cortex lesions (see (4 d survival, Cunningham, et al., 2004).

Phospholipase (A2)-directed inflammation likely contributes to most instances of neuron degeneration although prior to the present invention, there have been few in vivo tests of this idea. PLA2-related inflammation also plays a role in MS, as described elsewhere herein. An inhibitor of secreted phospholipase A2, namely, a nonapeptide fragment of human neuroprotective polypeptide DSEP, peptide CHEASAAQC (CHEC-9) (SEQ ID NO: 1), was discovered by the inventors (Cunningham, et al., 2002) and applied systemically for effective treatment of cerebral cortex lesions in rats (FIG. 18). CHEC-9 is described in detail in U.S. patent application Ser. No. 10/714,699, filed on Nov. 17, 2003, titled "Small survival-promoting/immunomodulatory peptide for treatment of brain damage, neurodegenerative disorders, and inflammatory disorders" incorporated herein in its entirety.

Both CHEC-9 and Lilly sPLA2 II inhibitor (LY311727) reduce human plasma sPLA2 activity by 60-70% with non additive effect. Both inhibitors may target the same sPLA2 enzyme pools (see FIG. 19).

CHEC-9 reduces systemic sPLA2 activity in humans. It has also been discovered that sPLA2 activity contributes to both acute and chronic neurodegenerative disorders. This is because it has now been shown that a nonapeptide sPLA2 inhibitor, CHEC-9, inhibits systemic sPLA2 activity and neuroinflammation, and importantly, rescues neurons when applied in an acute CNS lesion model (Cunningham, et al., 2004). CHEC-9 is a small mimetic of an endogenous human protein (DSEP) also discovered in by the inventors, and is suitable for development into a pharmaceutical. In the present invention, it has been discovered that the peptide also was effective in preventing EAE when treatment was begun post immunization at a time when systemic sPLA2 activity was estimated to be maximal. CHEC-9 also prevented or inhibited weight loss associated with the disease as well as the edema around the peripheral immunization site. Thus, there is now compelling evidence that CHEC-9 is an anti-inflammatory and neuroprotectve peptide with great potential for treatment of neuroinflammatory disorders.

In an aspect of the present invention, a simple, noninvasive test has been discovered for identifying early signs of inflammation, monitoring neurodegenerative inflammation, redirecting neurodegenerative diseases before symptoms appear, identifying high risk individuals, and identifying activities or situations (stress) which are damaging or potentially damaging to the nervous system.

The present invention is based, in part, on the discovery that complex biological fluids like urine can be successfully analyzed for enzyme activity and that the level of activity obtained is meaningful. For sPLA2, which is associated with a number of inflammatory events/diseases, including those which destroy the nervous system, it is demonstrated herein that different levels of activity could be detected in urine and correlated with those events/diseases. In some cases, increases in activity are found at early pre-symptomatic stages, as shown in animal models.

The invention is also based, in part, on detecting neurodegenerative inflammation by detecting and quantifying sPLA2 enzyme and/or nervous system specific proteins activity in a body fluid such as, for example, urine, sweat, saliva, and other fluids which have a detectable level of sPLA2 enzyme and nervous system specific proteins activity.

In another aspect, the invention provides a kit for detecting inflammation and neuron/axon degeneration/destruction in a body fluid, the kit comprising a sample comprising the body fluid and an antibody to detect an activity of an inflammatory enzyme and at least one of nervous system specific proteins in the sample. According to the invention, a kit can further comprise an indicator of inflammation and neuron/axon degeneration/destruction in the sample. An indicator can be any suitable media for demonstrating the presence of the inflammatory enzyme and at least one of nervous system specific proteins in the sample.

This invention is applicable to discovering and/or monitoring inflammatory destruction of neurons and axons associated with but not limited to the following: acute and chronic neurodegeneration including brain damage, spinal cord damage, trauma, stroke, peripheral neuropathy, neurodegenerative diseases such as Alzheimer's disease, Amyotrophic Lateral Sclerosis, Parkinson's disease, Multiple Sclerosis, mental retardation syndromes associated with progressive neuronal degeneration (e.g., cerebral palsies), and nonspecific anoxia (i.e., anoxia due to drowning, suffocation, etc.). It is also applicable to inflammation associated with vigorous exercise, sports injuries, prize fighting, inflammation associated with aging, and inflammation associated with any form of ongoing physical abuse.

This is because the present invention also demonstrates that a simple, non-invasive urinary assay can be used to characterize systemic PLA2 levels in MS patients. The same assay is also applied to rats following immunizations that produce EAE, in order to monitor levels of PLA2 in relation to the appearance of disease in this model. The present invention also demonstrates that when rats are treated with CHEC-9, a peptide inhibitor of sPLA2 activity that has been used previously to increase neuron survival and inhibit inflammation following acute lesions of the cerebral cortex, that CHEC-9 also ameliorates the symptoms of EAE. Because EAE has been shown to be an efficient model for human MS, the present invention therefore has direct applicability to the treatment of MS. That is, CHEC-9 can be used to ameliorate the symptoms of MS, based on the ability of CHEC-9 to inhibit the activity of PLA2 at the sites of MS disease in a patient.

In another aspect, the invention relates to daily or routine monitoring in "normal" individuals. In such patients, detection of an increase in sPLA2 and a loss of nervous system proteins may indicate the need for anti-inflammatory-therapy, such as, but not limited to, CHEC-9 (as described in detail elsewhere herein). Such treatment may provide beneficial effects to a patient including, but not limited to, prevention of Alzheimer's disease, prevention or treatment of dementia, and overall increased life expectancy. One advantage of this aspect of the invention is that because testing and/or treatment is only administered as needed, any downside or side effects of anti-inflammatory compound use is limited.

The appearance of various system specific proteins or fragments of nervous system specific proteins appearing in urine or other body fluids can be measured and correlated with the increased inflammation found in nervous system degenerative disorders including but not limited to Alzheimer's, MS, ALS, stroke, and trauma as well as other inflammatory disorders both neural and non-neural which actually damage central or peripheral nervous tissue including but not limited to overexertion in strenuous exercise, high prolonged fever, emotional stress (now known to have an inflammatory component), and serious burns.

These disorders will be accompanied by 1) increased urinary sPLA2 activity and 2) the possible appearance of nervous system specific proteins (and fragments of proteins) including but not limited to neurofilament protein (high, medium and low MW isoforms), beta tubulin isotype III (nervous system specific), oligodendrocyte specific protein (a component of CNS myelin and oligiodendrocytes), glial fibrillary acidic protein (structural protein in CNS astrocytes), myelin basic protein (a component of CNS and PNS myelin), NeuN (component specific to neuronal nuclei), as well as any other nervous system specific markers that are currently available or will be developed in the future.

In an embodiment of the invention, one or more of these proteins are assayed using standard quantitative Western Blotting assay since specific mono and polyclonal antibody probes for all these proteins are available commercially. In addition, any or all these probes can be used with multiple measuring instruments such as, for example, the BIORAD Multiplex Assay system (BioRad Inc, Hercules, Calif.) where the antibodies are attached to specifically coded beads for simultaneous measurement of several proteins in small volumes of bodily fluids like urine or serum.

In an embodiment, the invention provides for monitoring inflammation resulting in neuron/axon destruction by use of a procedure including an assay of a urine sample for an increase in a concentration of inflammatory enzyme (e.g., secreted phospholipase A2). Thus, inflammatory nervous system destruction can be detected at earlier stages so that therapy may be started early.

In an embodiment, the invention includes a method of monitoring inflammation by an increase in a concentration of inflammatory enzyme (secreted phospholipase A2 enzyme activity) and neuron/axon degeneration/destruction (monitoring levels of nervous system specific proteins) using an antibody based assay, such as, for example, Western blotting, ELISA or a multiplex assay in the urine or other bodily fluids. This method can be applicable to a variety of disorders (e.g., from stress, all neurodegenerative diseases, to prize fighting). The method is based on the discovery that active sPLA2 enzyme and fragments of nervous system specific proteins are excreted, and in the case of animal models of neurodegenerative diseases (like MS and ALS), and that they are secreted at the time of or before symptoms allowing an early intervention/detection.

Current practice relies on gross outward behavioral signs to (e.g. weakness, sensory deficits, cognitive difficulties) to indicate neuronal destruction under conditions of CNS inflammation. Inflammatory enzymes like sPLA2 might be measured in blood, but 1) this is an invasive procedure, whereas urine analysis is noninvasive, and 2) it would be difficult to also monitor neuron specific proteins (and their fragments) in blood to show neuron destruction. This difficulty is due to the high concentration of interfering proteins in blood and the very low concentration of interfering proteins in urine. The invention allows detecting the very first signs of this destruction in the context of an increase in inflammatory enzyme (secreted phospholipase A2), which can be measured directly in urine.

In the present invention, quantitative Western blotting methods to determine levels of neuron specific proteins (or fragments of these proteins) are combined with an enzyme assay for acute phase inflammatory enzyme sPLA2 of the same samples. These procedures are applied to urine in order to develop a simple noninvasive method to monitor neuron/axon destruction due to inflammation. Such a combined technique has not been applied to urine, or any other easily accessible bodily fluid (e.g., saliva). This combined technique was tested in several different models, among others: 1) urine sample of an adult male after vigorous exercise: both inflammatory enzyme activity and neuron-specific proteins are detectable in urine after 30 min, reduced by 6 hours and low at 24 hours post exercise); 2) urine samples of rats after spinal cord injuries (urine monitored at 6 hours, 24 hrs., and 4 days post contusion shows peak sPLA2 activity and neuronal protein in urine at 24 hrs.); and 3) urine samples from a mouse model of amyotrophic lateral sclerosis (G93/SOD1 transgenic mouse) which show ongoing elevations in urinary sPLA2 activity and neuron proteins in same samples suggesting that the procedure is useful in monitoring progressive neurodegenerative diseases (e.g., Alzheimers, Multiple Sclerosis (MS), etc.).

In an embodiment, the invention also uses urine samples from both animal models and humans with neurodegenerative disorders in order to demonstrate two important features of the invention: 1) the quantitative increase in urinary sPLA2 activity and of fragments of neuron specific proteins in the urine correlate with or precede the onset of neurological symptoms, and 2) that information provided by methods of the invention can be used to decide when to begin treatment of such patients with anti-inflammatory drugs.

Recent data from experimental autoimmune encephalitis (EAE, Multiple Sclerosis model) lend support that this approach may work as demonstrated herein. Following immunization of rats with the encephalitogenic compound (to give the rats EAE), sPLA2 activity was monitored in urine, and peaked prior to the appearance of EAE symptoms. Some rats were treated with sPLA2 inhibitor CHEC-9 at this time and this inhibitor prevented appearance of disease symptoms.

Figure 17:
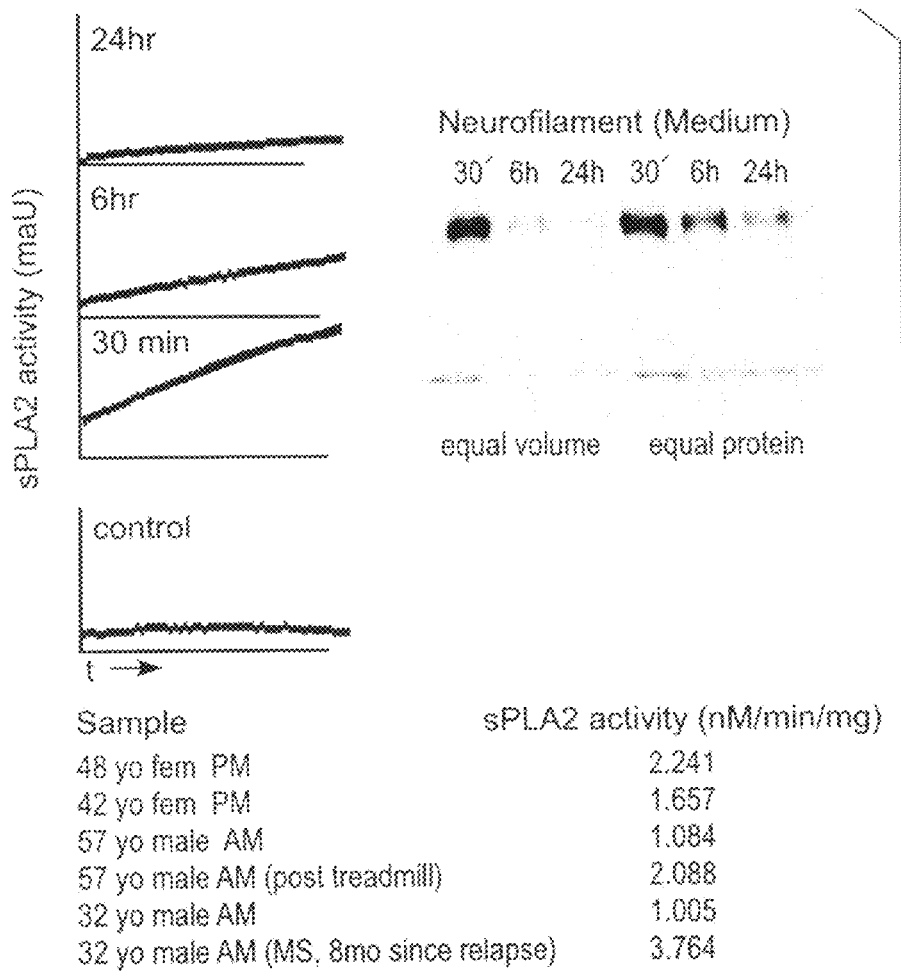
FIG. 17 is a graph and a picture of a gel demonstrating sPLA2 activity and neurofilament protein in urine at various times monitored following vigorous exercise.

FIG. 17 illustrates sPLA2 activity and neurofilament protein in urine at various times monitored following vigorous exercise (previously shown to be an inflammatory event). Both subjects recover in 24 hours. In neurodegenerative diseases, or in some activities (e.g., vigorous exercise, prize fighting), there may be persistent sPLA2 inflammation which may start even before symptoms appear. In an aspect of the invention, a test according to the methods set forth herein forms the basis for beginning treatment, identifying high risk individuals, or predicting damaging events of inflammation-related situations. Experiments conducted using the MS model (EAE) (FIGS. 12 and 7) demonstrate that the time course of sPLA2 activity after the immunization step which results in the MS like disease in subjects—sPLA2 activity peaks before symptoms, which is when treatment would start. Experiments conducted using the ALS model (G93a SOD1 transgenic) (FIG. 14) which has persistent elevation in urine sPLA2 activity throughout the symptomatic period (and probably before) demonstrate support for these potential applications. The application of methods of the present invention to such subjects has essentially cured the EAE rats with the sPLA2 inhibitor CHEC-9.

Figure 15:
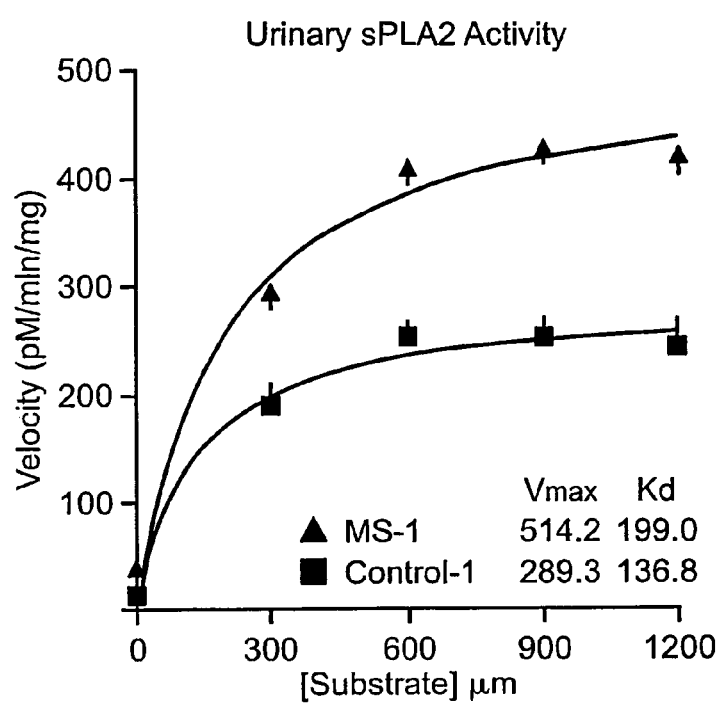
FIG. 15 is a graph depicting urinary sPLA2 activity, wherein urine samples were collected mid morning from a patient with Multiple Sclerosis (MS-1) and an age/gender matched healthy control (Control-1). The urine was sterile filtered and triplicate 25 µl samples were reacted with different concentrations of a thio-glycerophosphocholine substrate in the presence of Ca2+. This substrate is specific for sPLA2 activity. The reactions showed typical Michaelis-Menton enzyme kinetics under these conditions. The patient was in static phase (non relapsing), the last relapse occurring in October of 2004. The patient was not involved in any immunomodulatory therapy and neither patient nor control volunteer had engaged in strenuous physical activity or taken NSAIDs in the last 24 hrs.
Figure 16:
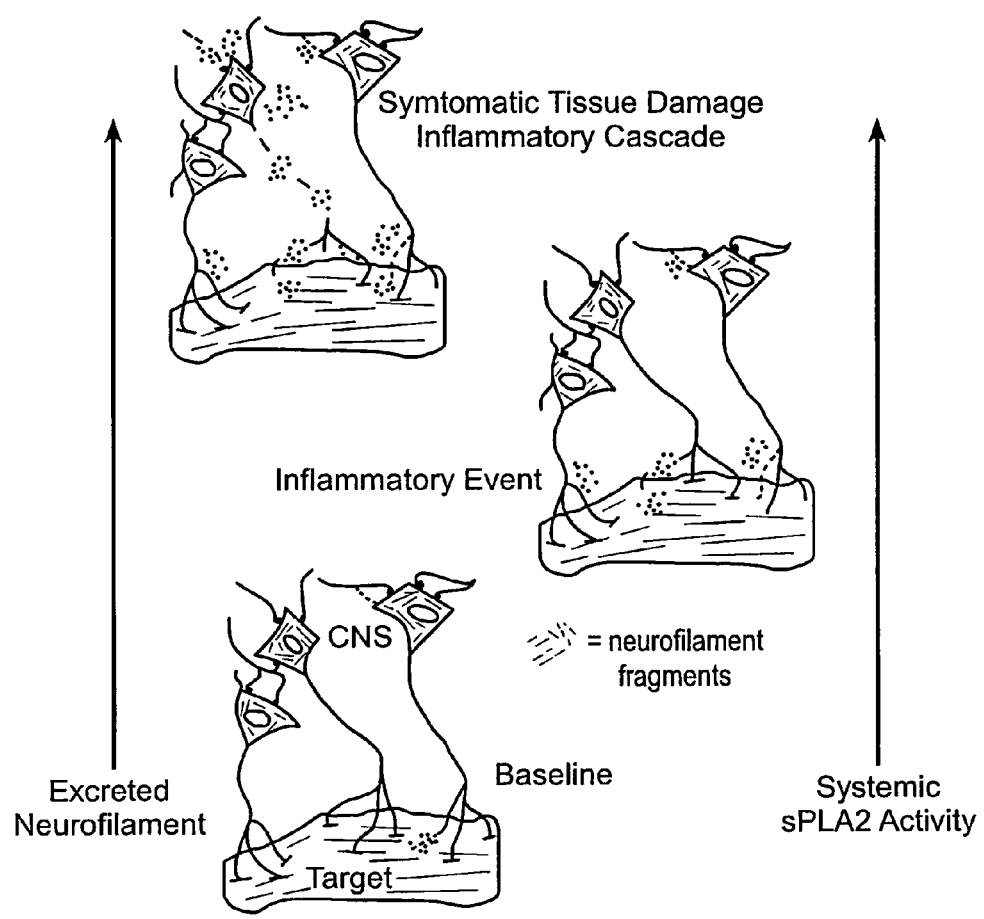
FIG. 16 is an illustration depicting the relationship between systemic sPLA2 activity and excreted neurofilament at different stages from a baseline (i.e., no inflammation) to an inflammatory cascade (i.e., a symptomatic tissue damage).

Urine samples from a multiple sclerosis (MS) patient and an age/gender matched healthy control were analyzed as shown in FIG. 15. This experiment demonstrates the activity in urine displays typical Michaelis-Menton enzyme kinetics using our assay system (thio-glycerophosphocholine substrate/Ca2+ initiated), and importantly, that the reaction has a maximum velocity and measurable affinity constant. This experiment validates the methods used in the present invention to monitor inflammation since the urine is indeed behaving like an enzyme.

The method of the invention can be applied to patients and animal models of Amyotrophic Lateral Sclerosis, Alzheimer's disease, spinal cord injury, and brain damage, among others. As will be understood by the skilled artisan when armed with the present disclosure, the invention is also applicable to the characterization of other inflammation-related conditions in a subject. With the subjects, the urinary measurements can be correlated with the standard performance scales used to measure severity of the nervous system disorder. For the animals, standardized behavioral testing methods can be used.

In another embodiment of the invention, a very stable peptide inhibitor of secreted phospholipase A2 (sPLA2) that is effective for systemic treatment of neurodegeneration associated with inflammation has been discovered. The peptide—called CHEC-9—inhibits aspects of the inflammatory cascade that follow damage to the CNS, and as a result, rescues neurons that would usually degenerate. Multiple Sclerosis is characterized by recurring CNS inflammation, axonal and cell degeneration, and subsequent appearance of neurological deficits. After repeated recurrences, the patients are often chronically disabled. Based on the remarkable properties of CHEC-9, and on recent reports concerning the role of sPLA2 activity in MS models, the invention set forth herein demonstrates that CHEC-9 can be used as therapy for Multiple Sclerosis. The invention also demonstrates preclinical testing of CHEC-9, including an ex vivo patient component, in order to demonstrate the feasibility of development of the CHEC-9 peptide as a pharmaceutical.

Therefore, in an embodiment, the present invention provides a method of treating MS in a patient having MS. In one aspect, the method includes administering to a patient having MS a CHEC-9 peptide. Methods of administration of a peptide will be understood by the skilled artisan when armed with the disclosure set forth herein. Such methods are also described in detail elsewhere herein.

In an aspect of the invention, CHEC-9 may be used as an anti-inflammatory or cell survival agent for a variety of disorders. This is because CHEC-9 is an uncompetitive sPLA2 inhibitor, as demonstrated herein. The advantage of an uncompetitive sPLA2 inhibitor for enzyme inhibition therapy is that, unlike competitive inhibitors, uncompetitive inhibitors are not rendered ineffective by the accumulation of unmodified substrate. Such conditions apply to several instances of neuroinflammation where there are cascading increases in sPLA2s and their substrates, both systemically and in the CNS.

It will also be understood, based on the disclosure set forth herein, that a CHEC-9-like peptide may also be useful according to the methods of the present invention as set forth herein. This is because the present invention teaches the structure and properties of a peptide—namely, CHEC-9—that is useful for detecting inflammatory conditions and treating such conditions, among other things.

The invention also includes an isolated polypeptide comprising a mammalian mutant CHEC-9 molecule. Preferably, the isolated polypeptide comprising a mammalian mutant CHEC-9 molecule is at least about 77% homologous to a polypeptide having the amino acid sequence of SEQ ID NO: 1, or some fragment thereof. Preferably, the isolated polypeptide is about 88% homologous, more preferably, about 99% homologous to SEQ ID NO: 1, or some fragment thereof.

The present invention also provides for analogs of proteins or peptides which comprise a mutant CHEC-9 molecule as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine; phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are mutant CHEC-9 peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the mutant CHEC-9 peptide of the present invention.

In another aspect of the invention, a CHEC-9 variant has one or more amino acids in addition to those present in CHEC-9. In another aspect of the invention, a CHEC-9 variant has one or more amino acids fewer than those present in CHEC-9. By way of a non-limiting example, a CHEC-9 variant may have 10 contiguous residues found in the larger DSEP protein from which CHEC-9 is derived.

A biological property of a mutant CHEC-9 protein should be construed to but not be limited to include the ability of the peptide to inhibit PLA2 activity. Because there is an inflammation component to MS, a biological property of a mutant CHEC-9 protein should also be construed to but not be limited to include the ability of the peptide to alleviate or eliminate one or more symptoms of MS.

The invention also encompasses the use of pharmaceutical compositions of an appropriate protein or peptide, mimetope, and/or peptidomimetic to practice the methods of the invention, the compositions comprising an appropriate protein or peptide, mimetope, and/or peptidomimetic and a pharmaceutically-acceptable carrier.

As used herein, the term "pharmaceutically-acceptable carrier" means a chemical composition with which an appropriate protein or peptide, mimetope, and/or peptidomimetic may be combined and which, following the combination, can be used to administer the appropriate protein or peptide, mimetope, and/or peptidomimetic to a mammal.

The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 µM and 10 µM in a mammal.

Pharmaceutical compositions that are useful in the methods of the invention may be administered systemically in oral solid formulations, ophthalmic, suppository, aerosol, topical or other similar formulations. They can be administered directly into the CNS or the peripheral nervous system intrathecally, intraventricularly, intraparenchymally, via direct injection, or via bioengineered polymers. In addition to the appropriate protein or peptide, mimetope, and/or peptidomimetic, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate hypericin derivative according to the methods of the invention.

In one embodiment of the invention, oral CHEC-9 administration prevents acute secreted phospholipase A2 (sPLA2) inflammatory response in mammals. Subcutaneous injection of gram-negative bacterial endotoxin (lipopolysaccharide, LPS) in rats gives rise to an acute inflammatory response that includes a transient 200-300% increase in plasma concentration of enzymatically active sPLA2. The increase is either mono or biphasic and begins within the first hour after LPS injection. If CHEC-9 is ingested 30 minutes after LPS treatment, (at time 0), this response is prevented. Similar results have been obtained with subcutaneous injections of CHEC-9, and following transient sPLA2 increases resulting from immobilization stress. CHEC-9 injected or ingested at later times during the LPS response, i.e., after the initial rise in active enzyme levels, accelerates the natural decline of enzyme in the plasma suggesting CHEC-9 is synergistic with endogenous inhibitory molecules.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to mammals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, rodents (including rats and mice), birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal, intraventricular, intraparenchymal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution, suspension, or slow-release polymer. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Another formulation is the activate ingredient incorporated in a slow-release polymer. Such polymers are well known in the pharmaceutical arts, and are detailed in, for example, U.S. Pat. Nos. (4,728,512; 4,728,513; 5,084,287; 5,285,186).

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention can be prepared, packaged, or sold in a formulation suitable for direct CNS administration. Such formulations may, for example, be in the form of liquid administered by an Ommaya reservoir, by intrathecal or intraventricular administration, by direct intraparenchymal injection, by slow-release polymers, or other such methods well known in the pharmaceutical and neurological fields.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to a mammal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to a mammal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Among other things, the present invention demonstrates that 1) Inhibition of systemic sPLA2 activity by injection of CHEC-9 will inhibit the progression of neurological symptoms and suppress the cellular immune response in rodent MS models; and that 2) sPLA2 activity is elevated in the blood and urine of patients with relapsing/remitting Multiple Sclerosis during active disease. CHEC-9 will inhibit this increased activity.

To this end, CHEC-9 and control treatment schedules are applied to Dark Agouti rats immunized with 1) myelin basic protein (moderate EAE) or 2) spinal cord homogenate (severe EAE). The rats are monitored daily for blood and urine sPLA2 activities and the development of EAE symptoms. Maximum levels of clinical disease are recorded and correlated with myelin/axonal degeneration, perivascular infiltrates, and immune cells including macrophages/microglia, granulocytes (neutrophils), and T-cells.

Additionally, the progress of the inflammatory response in rats with severe EAE is monitored with CHEC-9 and control treatment. This analysis includes quantification of the numbers and time course of appearance of degenerating axons and different inflammatory cells, as well as blood and tissue levels/activity of sPLA2, Thromboxane A2, Leukotriene B4 and Prostaglandin E2, and a panel of cytokines in multiplex assay system. The arachidonic acid metabolites (TBXA2, LTB4, PGE2) and many of the cytokines that are measured are known to be co-regulated in conditions of inflammation. These experiments therefore demonstrate the effects of CHEC-9 on the appearance and levels of downstream proinflammatory agents directed by arachidonic acid metabolism, as a further impetus for clinical development of this peptide.

In another embodiment, sPLA2 activity is measured in plasma and urine samples from patients with relapsing/remitting Multiple Sclerosis and compared to samples from healthy controls. The patient population can include individuals in both active and static disease states and include MS patients not on treatment studied at baseline, as well as those in defined treatment paradigms. EDSS and MSFC disability scores are measured for comparison with sPLA2 levels. A fraction of each blood sample is incubated with CHEC-9 to determine if the peptide inhibits sPLA2 activity in MS (as it does after treatment of whole blood of healthy volunteers). Downstream AA metabolites and multiple cytokines are measured in the plasma samples with and without prior CHEC-9 treatment.

Pre-Clinical and Clinical Development.

The purpose of the experiments set forth above is to generate evidentiary support for commercial development of a new peptide by adding to the growing body of evidence that sPLA2 is a worthwhile therapeutic target for neuroinflammatory disorders, and CHEC-9 is a new therapy. Multiple Sclerosis is one disease of interest for both theoretical and practical reasons. First, "acute phase" or early responders and innate immunity are presently of great theoretical interest in Multiple Sclerosis treatment. Secreted PLA2s, although largely overlooked as a therapeutic target for MS, are associated with acute inflammatory response rather than acquired immunity. In addition, the animal model for MS has a well-defined clinical and histopathological profile that appears in a relatively short period, compared to ALS or Alzheimer's models, for example. Therefore, more effective preclinical treatment paradigms are likely to be developed because overall duration of individual experiments is shorter. Clinical feasibility also represents an advantage for therapeutic development of CHEC-9. The experimental examples set forth herein are supported by a large patient population. Given the natural history of sPLA2 enzymes, it is follows that active (and perhaps static) disease states will be accompanied by elevated sPLA2 activity.

CHEC-9 Inhibits sPLA2 Activity in Human Plasma Samples after Treatment of Whole Blood Ex Vivo.

These experiments were conducted to determine whether CHEC-9 inhibits sPLA2 activity in human blood. Whole blood from 4 healthy volunteers (2M, 2F 36-57 yo) was collected by venipucture in Citrate Phosphate Dextrose (CPD) anticoagulant and divided for treatment of equal volumes with either CHEC-9 or vehicle (50 mM Tris, pH=7.4). Treatment was at 4° with gentle rocking for 2 hrs. Plasma samples were prepared by centrifugation and reacted with a glycerophosphocholine substrate specific for sPLA2 (Caymen Chemical). All samples treated with CHEC-9 showed inhibition of sPLA2 activity (50-80%). Final peptide concentration in plasma was 200-400 nM.

CHEC-9 Inhibition of sPLA2 Activity in Human Plasma Samples is Comparable to that of Lilly Designer sPLA2IIa Inhibitor LY31127.

Figure 3:
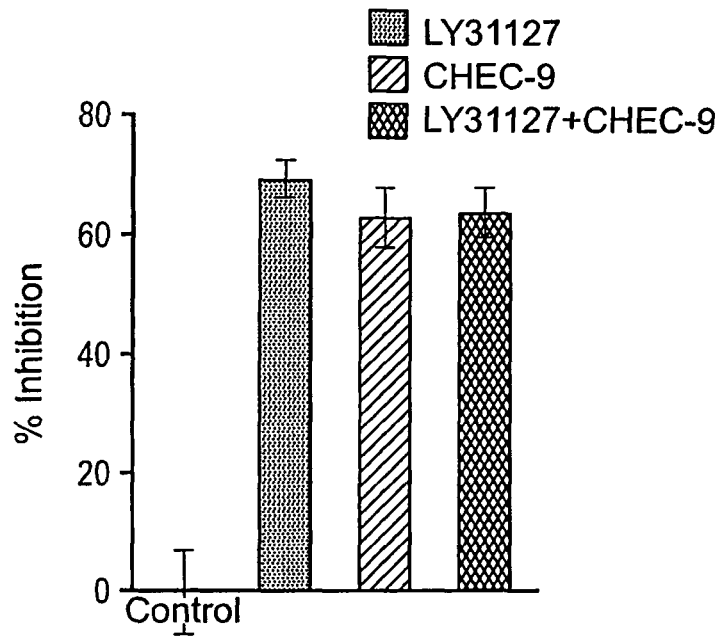
FIG. 3 illustrates how whole human blood was collected from a healthy 42 yr. old female volunteer and incubated at 4° for two 90 min periods with vehicle (control), CHEC-9 (0.4 μM) followed by vehicle (CHEC-9), LY31127 (5.0 μM) followed by vehicle (LY31127), or CHEC-9 followed by LY31127 (LY31127+CHEC-9). Inhibition was calculated by comparison with control velocity $[(1-V_{inh}/V_{con})\times100]$. Data shows the mean values for 4 enzyme reactions per condition. CHEC-9 and LY31127 at these concentrations appear to be equally effective inhibitors that are non-additive under these experimental conditions.
Figure 4:
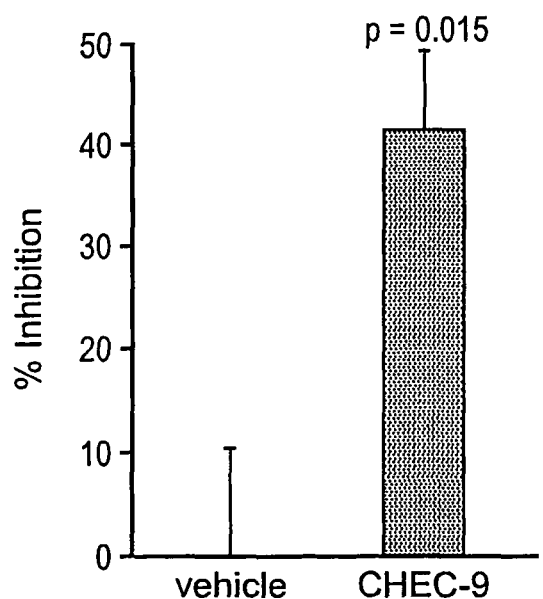
FIG. 4 illustrates that CHEC-9 or vehicle was delivered subcutaneously to 12 rats (0.4 mg/kg). Cerebral cortex membrane fractions were prepared as in previous studies (Cunningham, et al. 2000) except washed in 1M NaCl in buffer without protease inhibitors prior to use (see text). 7.0 mm$^3$ samples from each rat were equilibrated in DTNB (colorimetric reagent) and 50 mM Tris (pH=7.4), 0.1% triton X-100 for 20 min at 37°, and reacted with substrate in the presence of 2 mM Ca$^{2+}$ according to procedures described in Laboratory Methods. The average velocity 3 samples for each rat was measured. The percent inhibition was calculated as in FIG. 3, comparing vehicle and CHEC-9 injected rats (n=6 rats for each condition). P value is shown.

CHEC-9 was compared side by side with LY31227. This small molecule inhibitor was designed on the basis of sPLA2 IIa active site structure and is presently under consideration for non nervous system anti-inflammatory therapy. Both inhibitors were applied to whole human blood where the group II isoforms are predominant (FIG. 3). CHEC-9 and LY31227 gave similar results. The effect of the inhibitors was calculated by assuming the inhibition in the control samples was zero (see legend for FIG. 3). The effects of LY31227 and CHEC-9 were non-additive, suggesting either that they target a similar pool of enzyme in serum or there are complex interactions between the two inhibitors and/or their targets.

Systemic CHEC-9 Inhibits sPLA2 Enzyme Activity in Whole Cortical Cell Membranes of Saline-Perfused Normal Rats.

These studies were undertaken to determine whether systemic CHEC-9 would effect sPLA2 activity in CNS tissue of unoperated rats, thus suggesting that the peptide's influence was not blocked by the blood brain barrier. The results suggested that when whole membranes of saline perfused rats were tested, CHEC-9 injections produced significant inhibition of sPLA2 activity under the conditions used herein. Tissue preparations from cerebral cortex homogenates of normal rats that had been injected with 0.4 mg/kg CHEC-9 were tested, at the dosage of the peptide used in the lesion studies. These extracts were prepared as in previous studies (Cunningham, et al., 2000) and included cytosol, CHAPS solubilized membranes, with and without a prior salt wash, and whole membranes, i.e. nonsolubilized, after salt wash. In addition, protease inhibitors were added or omitted at different stages of these preparations. The most consistent sPLA2 activity and CHEC-9 inhibition was found in salt washed whole membranes without protease inhibitors in these final samples, compared to for example, CHAPS solubilized membranes with protease inhibitors. This procedure has therefore been used in all recent studies. Pete, et al., (1996) report that the protease inhibitor PMSF also inhibits PLA2 activity.

CHEC-9 Treatment of Purified Cell Populations.

Purified cerebral cortex neurons and purified microglia were each treated with CHEC-9. The microglia were purified on a rotary shaker from an astrocyte feeder layer after 10 days in vitro. Microglia in vitro are notoriously unstable morphologically, usually either spreading out into a large flat cell or becoming fusiform and forming long slender processes. Without treatment they continue to divide in culture. After activation with a variety of agents, the cells 'deramify' into round ameboid microglia, so this behavior is similar to their morphological response after activation in vivo (Bohatschek, 2001; Lombardi, et. al., 1998; Kloss, et. al., 2001). In addition, these morphological changes correlate with upregulation of a variety of proinflammatory cytokines and inflammatory mediators. Bacterial lipopolysaccharide, sometimes in combination with interferon, was used for activation and microglia. In the experiments shown in FIG. 5, LPS (25 ng/ml) was added to the cultures followed (20 min later) by CHEC-9 to a final concentration of 0.1 nM. After an additional 48 hrs, it was found that the numbers of microglia in both peptide-treated and vehicle-treated cultures were similar, but almost twice as many cells in control cultures had a round ameboid morphology (FIG. 5), suggesting CHEC-9 interferes with activation of the microglia in vitro.

CHEC-9 Promoted the Survival Cortical Neurons Developing In Vitro.

The neurons were from 1 day-old rats and developed in vitro for 4 days at low density ($1 \times 10^4$ cells/cm$^2$). Twenty-four hours after plating, the medium was changed and CHEC-9 was included in the new medium of some cultures at a concentration of 0.1 nM. When the cultures were terminated, 80-95% of the surviving cells were stained with the TUJ1 antibody against neuronal specific tubulin. The vast majority of contaminating cells were GFAP+ astrocytes. At this density of plating, and in the absence of an astrocytic feeder layer, there was widespread death of the neurons in both groups of cultures after 4 days. CHEC-9 treatment however resulted in a highly significant sparing of the TUJ1 positive neuronal cells. FIG. 6 shows representative data from one of four separate experiments, each involving several cultures and each showing a several fold increase in the numbers of surviving neurons.

CHEC-9 Treatment of Experimental Autoimmune Encephalitis.

A study was conducted using 10 Dark Agouti rats immunized bilaterally in the foot pads with guinea pig myelin basic protein emulsified with complete Freund's adjuvant. As described by others (Milicevic, et al., 2003), this procedure in DA rats induces a moderate but consistent EAE response after 10-15 days which is characterized by tail and limb paresis/paralysis. Experiments lasted 18 days following immunization, during which time the rats were weighed and scored for clinical disease daily. Post-immunization (PI) changes in sPLA2 activity in urine was monitored as a potential guide to an appropriate CHEC-9 treatment regimen (FIG. 7). Treatment with CHEC-9 or vehicle was begun on day 5 PI when there was a significant peak in urinary aPLA2 activity. The rats were then treated for 10 days with 60 µg peptide (first day) and 30 µg (subsequent days) in 200 µl delivered subcutaneously (~0.4 and 0.2 mg/kg respectively). For blinded treatment and observations both the animals and syringes were coded. The sPLA2 response at 4-8 days PI was followed by decline of average activity over the next four days. This drop in activity was significant for CHEC-9 treated rats but not vehicle treated rats (FIG. 7).

Urine samples were also prepared for SDS page and immunoblotting in order to assay for neurofilament. These experiments represent an attempt to provide a non-invasive measure of neuron/axon loss by semi-quantitative Western analysis. So far the analysis has been limited to the usually 160 kD neurofilament M. Although the specific fragments of this protein that appear in urine are variable depending on the model, consistent increases were found in one or more of these fragments under conditions where neuron/axon death might be expected.

Foot edema caused by MBP/CFA injections was measured. These blinded measurements were made on PI day 10, after 5 days of treatment. Rats treated with the peptide had reduced or no swelling of the feet. Since foot thickness was not measured continuously post immunization, the relative contributions of inhibition and reversal of the edema by CHEC-9 are not clear at present. Nonetheless, these experiments suggest that CHEC-9 has peripheral anti-inflammatory/immunosuppressive properties that may contribute to its effectiveness in the present experiments, and in other applications and indications.

Figure 9:
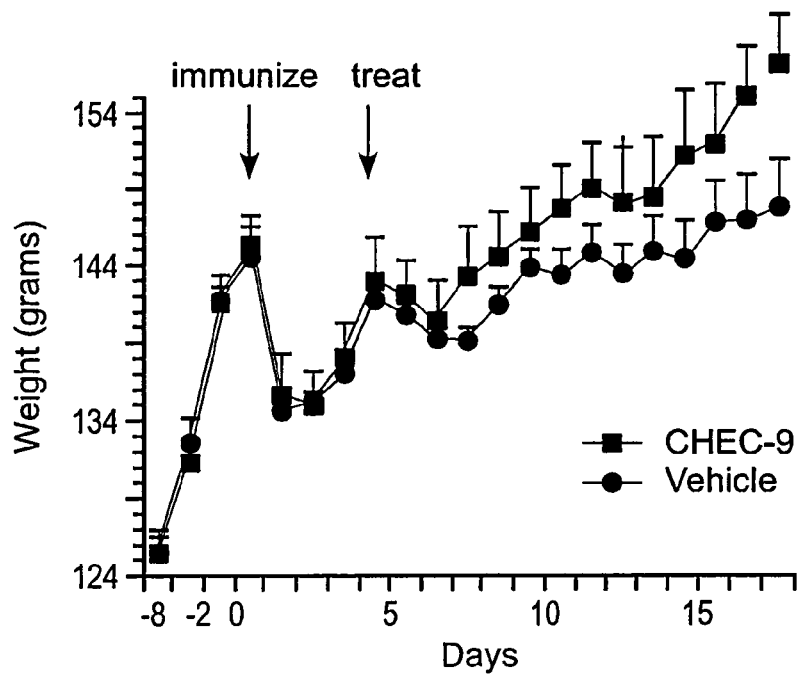
FIG. 9 shows the body weight of DA rats immunized with guinea pig myelin basic protein in CFA. The rats added weight normally prior to immunization after which there was an expected precipitous decline. CHEC-9/vehicle treatment began 5 days after immunization. CHEC-9-treated rats add body weight at a significantly higher rate than the vehicle-treated rats during the period when the latter developed EAE symptoms.
Figure 10:
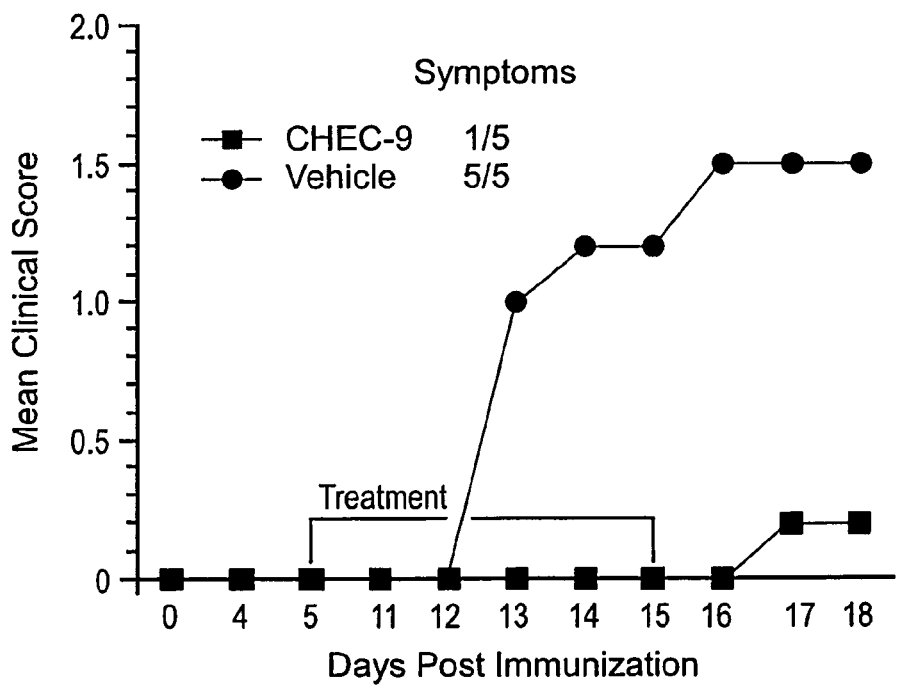
FIG. 10 shows the development of EAE symptoms in DA rats immunized with guinea pig myelin basic protein/CFA. The rats were treated with CHEC-9 or vehicle for 10 days starting on PI day 5. They were scored daily on a 0-4 EAE scale (see Methods) by two separate investigators who did not know the experimental categories. All vehicle treated rats developed symptoms, 3 with hindlimb involvement. One of the CHEC-9 treated rats developed a weak tail on PI day 17.
Figure 13:
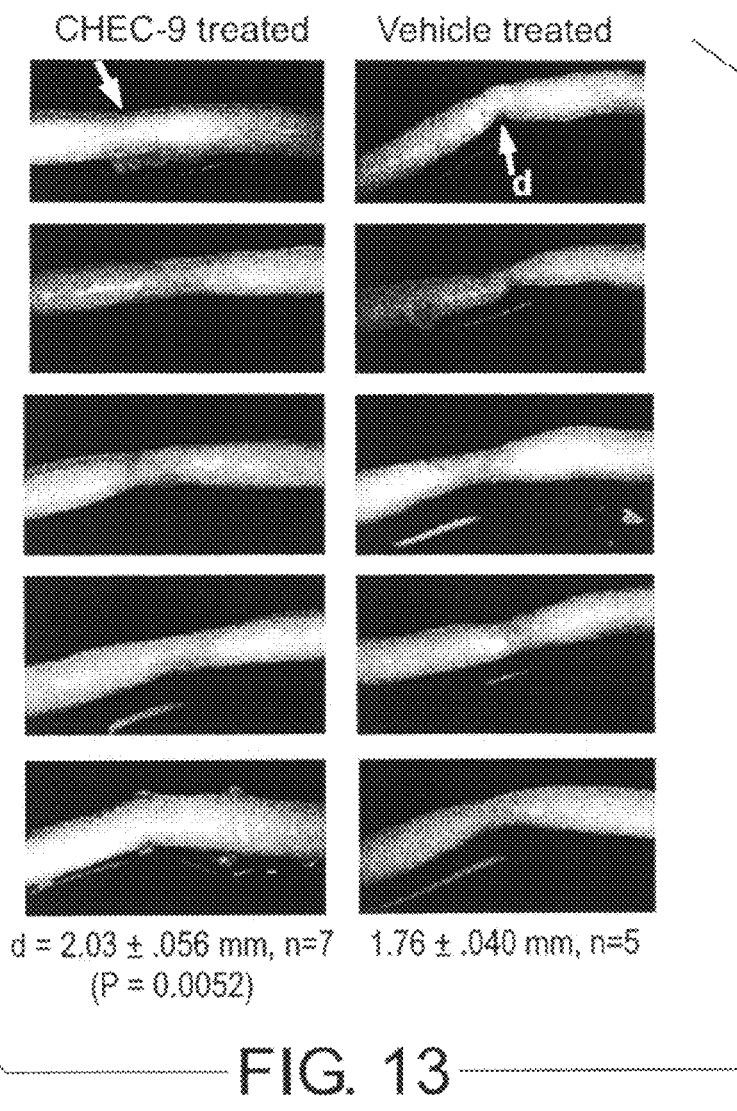
FIG. 13 shows CHEC-9 treatment of contusion injury to the spinal cord. Contusion of the spinal cord was with the MASCIS impact device set at 25 mm weight drop. The peptide was delivered at 0.4 mg/kg subcu. 20 minutes after the lesion and the rats were sacrificed 12 days later. Measurement of whole cord diameter (d) at the epicenter of the contusion reveals a significant sparing after CHEC-9 treatment. Five of the 7 CHEC-9 treated rats are shown above opposite all 5 vehicle treated rats. All rats were used for blinded measurements and for the statistical analysis. Histological processing of the spinal cords is in progress.

FIGS. 9 and 10 show the results of daily weight measures and EAE clinical scoring in the pilot study. These data were collected in an experimentally blinded manner. The results of both measurements showed that CHEC-9 treatment prevented the onset of disease in all but one rat that had late onset tail weakness. The rate of weight gain after CHEC-9 treatment was accelerated in the peptide treated rats.

One spinal cord was sectioned from each group through the region of the conus medullaris and stained for Nissl-myelin. The peptide treated rat (#411) showed no deficits and the vehicle treated rat (#410) scored 2.5 (tail flop, one paralyzed and on paretic limb). There were marked obvious differences in the histology of caudal spinal cord between these two rats—several millimeters of the caudal-most spinal cord was severely atrophic in rat 410. The sections revealed that there was extensive cell shrinkage and/or small cell invasion as well large regions of dense degenerating myelin (FIG. 11). Rat 411 had small areas of degenerating myelin but little apparent atrophy either of the cord or of the cells. These results are consistent with the clinical scores of the two rats.

Experiments using spinal contusion and ALS models of neurodegeneration were conducted in order to define the contribution of sPLA2 enzyme activity to the inflammatory component of these disorders and to further test the efficacy of CHEC-9. Increased urinary and/or serum sPLA2 activity was detected during a period of expected neuron death. In these studies, urinary levels of proteolytic fragments of neurofilament M were detected as a potential monitor of neuron/axon destruction. Interestingly, however, each of the three models has a relatively characteristic pattern of NF(M) fragment accumulation at a time when neuron/axon loss might be predicted.

For the spinal contusion model, CHEC-9 has recently been applied with a single injection (0.4 mg/kg) 20 minutes after the surgery, which is the same treatment procedure used in the study of cerebral cortex lesions (Cunningham, et al., 2004). The diameters of the fixed cords at the epicenter of contusion in rats that survived for 12 days were measured. There is significant sparing of tissue in this region after CHEC-9 treatment. The symptomatic G93A/SOD1 transgenic mouse also shows elevated sPLA2 activity. This model is characterized by a predictable pattern of motor neuron loss and motor deficits beginning around 80 days of age. Significant increases in urinary sPLA2 activity at this age as well as at a late symptomatic stage (~130 days). In these experiments, the samples from mice of different ages and genders were pooled for the analysis, the latter grouping because of gender differences in the timing of the disease in this colony. All groups gave similar results with reference to sPLA2 activity. Immunoblots for NF (M) in the urine of the mice showed elevated levels of this protein in symptomatic mice but suggest that a different NF fragment predominates in this particular model (FIG. 14).

Urine and Blood Collection.

Rats, housed under uniform light cycle and temperature conditions, are placed in metabolic cages with water ad libitum starting at 9:00 AM and are removed after the first urination (usually within 2 hours). Typical volume is 0.8-2 ml. The samples are sterile filtered in spin cups (0.22 µM) and frozen. Blood (0.6-1.2) ml is collected under a heating lamp by a small tail nick after application of topical anesthetic. Serum is also prepared from blood moved by cardiac puncture prior to perfusion for the whole tissue and histological studies. Serum is prepared after clotting by centrifugation twice followed by sterile filtration. The same procedure is used for plasma collected in CPD anticoagulant.

Histology/Immunocytochemistry.

Animals are anesthetized with Nembutal (100 mg/kg i.p., Abbott Laboratories) and perfused transcardially with 200 ml of physiological saline followed by 500 ml of ice cold 4% paraformaldehyde in 0.1 M phosphate buffer (pH 7.4). The spinal cord is dissected out and immersed for 2 hours in 0.1 M phosphate buffer (PB) at 4° C. followed by cryoprotection in 30% sucrose for 3-5 days. The region of the spinal cord from beginning of the lumbar enlargement to the filum terminale is removed and bisected into two blocks (one rostral, one caudal) that are cut cut sagittally at 20 µm using a cryostat. Then, 10-14 sets of serial sections are obtained (sampling is every 100 µm) through the spinal cord in each block which is adequate for the analyses proposed below. Sections are mounted onto gelatin-coated slides and processed for histological or immunocytochemical staining using standard protocols from our laboratory.

The following analyses are performed on individual sets of serial sections: 1) Conventional Nissl-Myelin staining is used to quantify the overall area of caudal spinal cord involved in the EAE lesion 2) Conventional Hemotoxylin and eosin staining to quantify the number of perivascular infiltrates in the area of involvement. 3) Double immunofluorescent staining for amyloid precursor protein (goat polyclonal) and normal neurofilament (mouse monoclonal to NFM or NFL). 4) Double immunofluorescent staining for CD4+ T cells and monocytes (CD4 antibody is direct ALEXA-647 conjugate and ED-1 (macrophages/microglia) is direct FITC conjugate). These two probes are used together because the anti-CD-4 mAb reacts weakly with monocytes. 5) Double immunofluorescent staining for rat granulocytes (mouse monoclonal) and oligodendroglial specific protein (rabbit polyclonal).

TABLE 1

Antibodies and Kits

| Target | Type | Use/Dilution | Source |
|---|---|---|---|
| Neurofilament Medium (NFM) | Monoclonal | IH: 1:100 IB: 1-3000 | Chemicon |
| Mouse anti-rat CD4 T cells | Mouse Monoclonal-Alexa 647 | IH: 1:100 | Serotec |
| Neuronal Class III Beta Tubulin (TUJ1) | Mouse monoclonal | 1:200 | Covance |
| OSP Oligodendrocyte marker | rabbit polyclonal | IB: 1:4,000 | ABCAM |
| APP marker for acute axonal injury/degeneration | Goat polyclonal | IH: 1:50 | Chemicon |
| Macrophages/microglia CD68 | mouse monoclonal: ED1-FITC | IH: 1:100 | Serotec |
| Rat granulocytes MOM/3F12/F2 | Mouse monoclonal | IH: 1-50 | Serotec |
| Thromboxane A2 | ELISA kit | assay | Assay Designs |
| Prostaglandin E2 | ELISA kit | assay | Caymen Chemical |
| Leuktriene B 4 | ELISA kit | assay | Assay Designs |
| Secreted PLA2 | ELISA kit | assay | Caymen Chemical |

IH = immunhisto/cytochemistry IB = Immunoblotting

The parameters of interest in the sections are quantified Leica DMRBE epifluorescent microscope with after capture on attached Sensys model 1401 CCD camera/LCD filter system (Biovision Technologies) using IPLABS software (Scanalytics, Inc.). All quantification is done on blind coded slides. The available software provides all necessary macros for the analyses proposed, from tracing the caudorostral and mediolateral extent of myelin degeneration and infiltrates to quantifying the densities and extent of normal axons, dystrophic axons (positive for APP) and specific immune cells. The quantification can be accomplished by means of overlay grids appearing on captured images. The parameters of interest in the sections are quantified Leica DMRBE epifluorescent microscope with after capture on attached Sensys model 1401 CCD camera/LCD filter system (Biovision Technologies) using IPLABS software (Scanalytics, Inc). All quantification is done on blind coded slides. The available software provides all necessary macros for the analyses proposed, from tracing the caudorostral and mediolateral extent of myelin degeneration and infiltrates to quantifying the densities and extent of normal axons, dystrophic axons (positive for APP) and specific immune cells. The quantification of the axons is accomplished by means of overlay grids appearing on captured images. If cell body counts are made from populations with non uniform diameters, we use the dissector method or apply appropriate corrections as in numerous previous studies. Cytosolic and membrane fractions are prepared by ultracentrifugation in PBS perfused rats as in previous studies (Cunningham, et al., 2002). It is fully automated for tissue, and serum and kits are available for simultaneous measurement of several cytokines of interest in rat EAE and human MS.

PLA2 enzymes hydrolyze 2-acyl bond of 3-n-phosphoglycerides. The assay used includes the use of 1,2-bis(heptanoylthio)glycerophosphocholine (specific for sPLA2, Caymen Chemical) as a substrate. In this compound, a sulfur forms this bond and upon cleavage there is a free sulfhydryl which is detected using DTNB. Serum or urine once equilibrated in DTNB is unreactive in this assay (in the absence of substrate and $Ca^{2+}$), CHEC-9 is unreactive in the absence or presence of substrate, and the substrate is stable in the absence of plasma or purified enzyme. Furthermore, the use of such artificial substrates instead of natural substrates is preferred for inhibitor studies since disruption of interfacial organization (the enzyme acts at the lipid interface on biological membranes) may appear as true enzyme inhibition (Mihelich, 1997). These substrates are also preferred over assays that involve arachidonic acid generation because of the several different possible sources of AA (Cummings, et al., 2000). The assay has been modified (from the procedure recommended by Caymen) using a simple salt solution (0.1M NaCl in 50 mM tris pH7.5) and 2 mM $Ca^{2+}$, the latter reagent is used to initiate the reaction with a multichannel pipette immediately after addition of substrate. A 10-15 μl sample of plasma, or 25 μl sample of urine clearly shows highly significant changes in activity under conditions of nervous system inflammation. A temperature controlled ELX-808 microplate reader is used, with agitation and fully programmable kinetic readout that is analyzed by Delta Soft software. The data can be converted to moles/min/vol(wt) using the extinction coefficient for DTNB at 415 nm of 13,600/mole/cm-1. Kinetic parameters can be then determined using non-linear regression software from Graphpad (Cunningham, et al., 2004). However, a simple steady state rate calculation is used in the presence of excess substrate which provides a consistent and reliable estimate of the activity of the biological fluid under study. Activity of serum samples is expressed per volume of serum due to the consistently high protein content. For urine, preliminary observations of raw velocity data (OD/min) of a constant volume can be used especially where relative measures are required (e.g. time course, CHEC-9 inhibition). Regardless, sPLA2 activity data in urine is always is always expressed per total protein content. The pattern of activity curves in the animal experiments, so far at least, has been similar with either method perhaps due to the uniform urine collection procedures that we have adopted. Peptide Preparation: CHEC-9, scrambled, and substituted peptides, are made at the Protein Chemistry Facility, Department of Pathology, University of Pennsylvania. These are HPLC purified and the molecular weight is confirmed by Mass Spectrometry. We redissolve and dry peptide samples twice upon receipt to further remove any solvents used in production. The peptides are crosslinked as described in Cunningham, et al 2004, and their structure is confirmed using Mass Spectrometry.

sPLA2 activity is also measured in plasma and urine samples from patients with relapsing/remitting Multiple Sclerosis and compared to samples from healthy controls. The patient population consists of individuals in both active and static disease states and includes MS patients not on treatment studied at baseline, as well as those in defined treatment paradigms. EDSS and MSFC disability scores are measured for comparison with sPLA2 levels. A fraction of each blood sample is incubated with CHEC-9 to determine whether the peptide inhibits sPLA2 activity in MS (as it does after treatment of whole blood of healthy volunteers). Downstream AA metabolites and multiple cytokines are measured in the plasma samples with and without prior CHEC-9 treatment.

Studies of PLA2 Activity in MS Patients and Potential Role of CHEC-9 in Therapy.

Forty-four patients with a diagnosis of relapsing/remitting Multiple Sclerosis provided urine samples for the study (Table 2).

Healthy controls were recruited by advertisement. The Institutional Review Boards of Drexel University and Graduate Hospital of Philadelphia approved the study and informed consent was obtained from all subjects. Twelve of the patients presented with active disease at the time of sample collection, which was defined as a change of one or more points on the functional neurologic status score in the absence of fever or infection. Therapies noted in Table I were interferon beta-1a (Avonex®, Biogen, 30 μg/week I.M.) or glatiramer acetate (Copaxone®, Teva Pharmaceutical Industries 20 mg/day, S.C.). Subjects with peripheral infections or inflammatory disorders, or those using anti-inflammatory drugs within the 24 hours prior to sample collection, were excluded from the study.

EAE Production and Analysis.

The animal experiments were conducted under the auspices of an approved IACUC protocol from Drexel University. All personnel involved were experimentally blinded for all procedures. Mild to moderate EAE was induced in 20 female Dark Agouti rats (130-150 g) by bilateral foot pad immunizations of 100 μg guinea pig myelin basic protein in saline emulsified with Complete Freund's Adjuvant. The rats were weighed and scored for EAE symptoms daily using a 1-4 rating scale for clinical disease (1-tail drop, 2 hind limb paresis, 3 hind limb paralysis, 4 moribund). A score of 2.5 was given for complete paralysis of one hind limb, which was the most severe disease encountered in this experimental system. The experiments lasted 18 days following immunization, after which the rats were perfused with 4% paraformaldehyde in 0.1M phosphate buffer and their spinal cords removed for histology.

Urine Collection and CHEC-9 Treatment.

Urine was collected in metabolic cages from all rats starting 1-2 days before immunization and then every other day for 18 days. CHEC-9 treatment started 5 days after immunization during the rise in urinary PLA2 activity. Treatment consisted of a subcutaneous injection of 60 μg CHEC-9 in clear DMEM vehicle on the first day, followed by daily 30 μg doses for 9 days. CHEC-9, CHEASAAQC (SEQ ID NO: 1), was made by Celtek (Nashville, Tenn.), purified and crosslinked as described previously.

PLA2 Enzyme Activity.

Twenty-five μl samples of (0.2 μm) filtered urine were reacted with 1,2-bis(heptanoylthio)glycerophosphocholine, a substrate for PLA2s with the exception of cPLA2 and PAF-AH (Caymen Chemical, Ann Arbor Mich.). Reaction buffer consisted of 50 mM tris, 0.1M NaCl (pH=7.4) containing 1 mM DTNB (Ellman's reagent) and 2 mM $CaCl_2$. Rates and kinetic parameters were determined by a Deltasoft (Princeton N.J.) supported ELX 808 reader (Biotek, Burlington Vt.) and non-linear regression software from Graphpad (San Diego Calif.), and expressed relative to total protein in the samples. Selected urine samples were dialyzed in 1 kD membranes against 20 mM tris and prepared for Western blotting as in previous studies. SDS PAGE prior to blotting was under reducing conditions. Blots were reacted with a polyclonal antibody directed against human sPLA2 IIa (Caymen Chemical). All data comparisons were by a two-tailed Mann Whitney test or nonparametric (Spearmann) linear correlation.

TABLE 2

Range of MS patient data.

| Group | n (F/M) | Age yrs ± sd | MS Onset yrs ± sd | MS Duration yrs ± sd | βIF | GA | None |
|---|---|---|---|---|---|---|---|
| Active | 12 (8/4) | 38.2 ± 9.5 | 29.5 ± 8.9 | 7.3 ± 4.5 | 9 | 1 | 2 |
| Stable | 32 (25/7) | 43.6 ± 8.1 | 33.4 ± 8.6 | 10.6 ± 9.3 | 15 | 3 | 14 |
| Control | 14 (9/5) | 37.5 ± 9.0 | — | — | — | — | — |

F/M = female/male; βIF = beta Interferon; GA = glatiramer acetate; sd = standard deviation Other assays were conducted at ambient temperature (22-25°) using a Victor 3 fluorescent reader (Perkin Elmer, Nutley N.J.). The substrate was 1-Palmitoyl-2-Pyrenedecanoyl Phosphatidylcholine ("10-pyrene", Caymen Chemical, Ann Arbor Mich.) a substrate for all calcium dependent PLA2s with the exception of cPLA2 and PAF. The substrate (supplied in chloroform) was dried under a nitrogen stream, quickly dissolved in ethanol, and stored at −20° prior to use. Substrate solutions were prepared in reaction buffer consisting of 50 mM tris (pH=7.4), 0.1M NaCl, 2 mM $CaCl_2$, 0.25% fatty acid-free albumin (Sigma) and the CHEC-9 peptide at the indicated concentrations. CHEC-9 (CHEASAAQC) (SEQ ID NO: 1) was synthesized by Celtek, (Nashville, Tenn.), purified and cross-linked as described previously (see Cunningham, et al 2004), and aliquots stored in tris buffer or DMEM vehicles at −80°. The 10-pyrene substrate forms phospholipids vesicles in aqueous solutions, and upon hydrolysis, releases 10-pyrenyldecanoic acid. This product is fluorescent in the presence of albumin and was measured at 350 nm excitation, 405 nM emission. Plasma samples were 20% final concentration in the reaction mixture, and all enzyme reactions were initiated with the addition of the substrate solution to the sPLA2 containing samples. Kinetic parameters including the properties of CHEC-9 were determined by measuring the initial velocities ($V_o$) of enzyme reactions (within 1 minute of initiation). For experiments in which active sPLA2 enzyme concentration was measured in plasma samples from peptide-treated rats, we used a single substrate concentration and measured the steady-state rate of the enzyme reaction for 30 minutes. This rate is proportional to the concentration of active enzyme in the plasma if product formation during this period is linear with respect to time. In most experiments, relative fluorescent units (RFU) were converted to product concentration using a pyrenyldecanoic acid standard curve (Molecular Probes, Eugene, Oreg.). For plasma, the background fluorescence of the plasma was not subtracted, but this did not effect the velocity measurements. Individual reactions were carried out in duplicate or triplicate and kinetic curves were produced using 5-6 substrate concentrations, with or without peptide, reacted simultaneously. Representative Lineweaver-Burke plots and nonlinear regression analyses are presented in Results, only after repeating an experiment 5 or more times with the same result, i.e., the direction of change of Km and Vmax was the same following inhibitor treatment, and $K_i$ was less than 100 nM. Km and Vmax were determined with nonlinear regression software (Prism) from Graphpad (San Diego, Calif.).

Results of MS and EAE Studies.

Figure 22A:
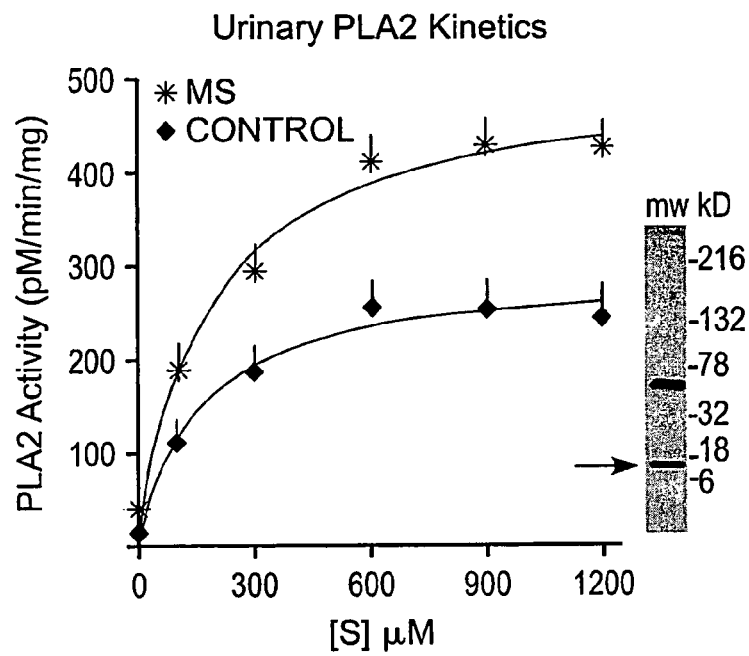
FIGS. 22A and 22B, is a series of graphs depicting urinary PLA2 enzyme activity in MS patients and controls.
Figure 22B:
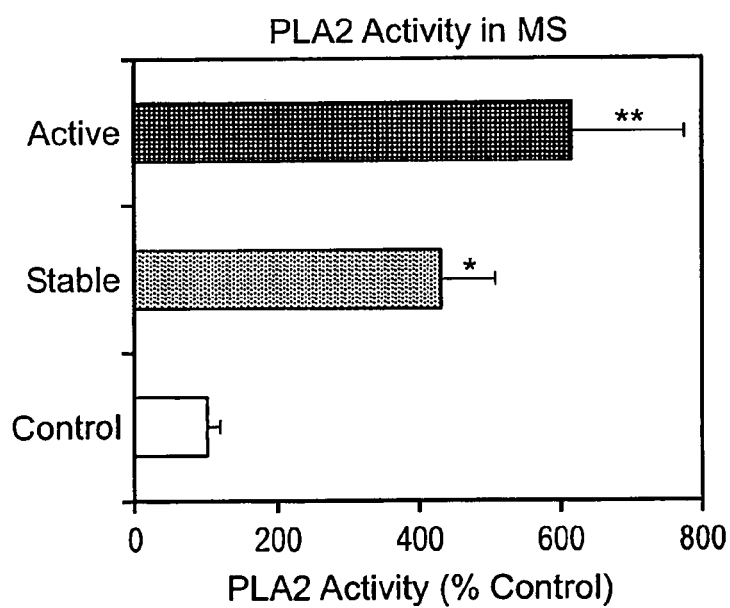

Filtered urine follows typical Michaelis-Menton reaction kinetics indicating that measurements of velocity at saturating substrate concentrations are proportional to the concentration of active enzyme present in the sample (FIG. 22A). The average sPLA2 activity is significantly elevated in the urine of patients with both active and stable MS (FIG. 22B). The mean activity was higher in relapsing patients compared to non-relapsing patients although the difference did not reach statistical significance (p=0.107). Interestingly, there was no difference in the mean activity of stable patients receiving no treatment and those treated with beta interferon (mean 393±130% of control n=15, versus 409±98% s.e.m., n=14, p=0.585). However these patients are heterogeneous with respect to PLA2 levels as suggested by the high variances in the measurements. Importantly, PLA2 activity does not correlate with total urinary protein in any group, so it is unlikely that the patients simply leak more PLA2 because of some previously unrecognized deficit in renal function (p values for protein-PLA2 correlation, Active=0.572; Stable=0.350; Control=0.885). We also found that dialyzed and concentrated samples (200 μg total protein) were immunoreactive for the 14 kD group IIa PLA2 species, suggesting that whole PLA2 molecules (at least for this isoform) are excreted (FIG. 22A, inset).

Figure 23A:
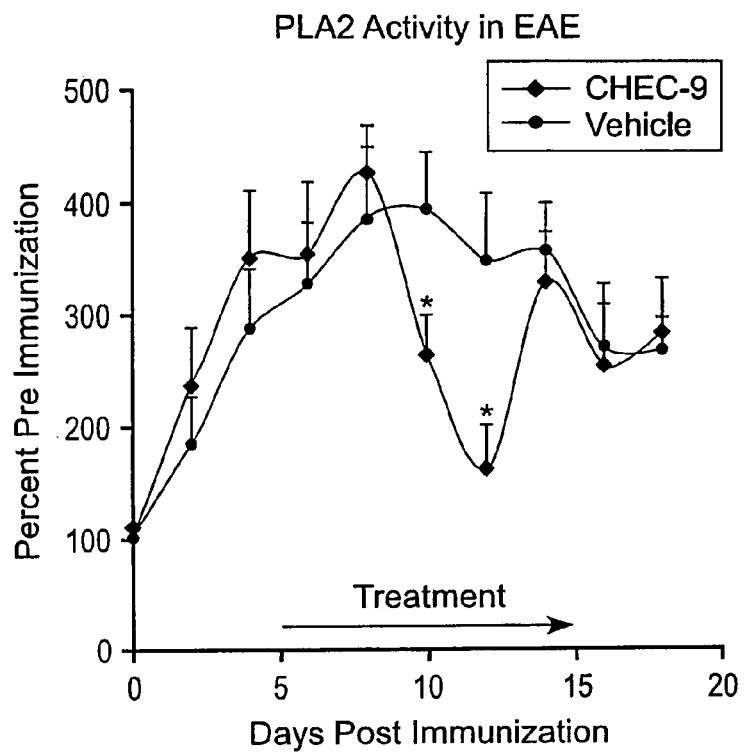
FIGS. 23A and 23B, is a series of graphs depicting PLA2 activity and clinical disease in experimental autoimmune encephalomyelitis (EAE) rats treated with sPLA2 inhibitor.
Figure 23B:
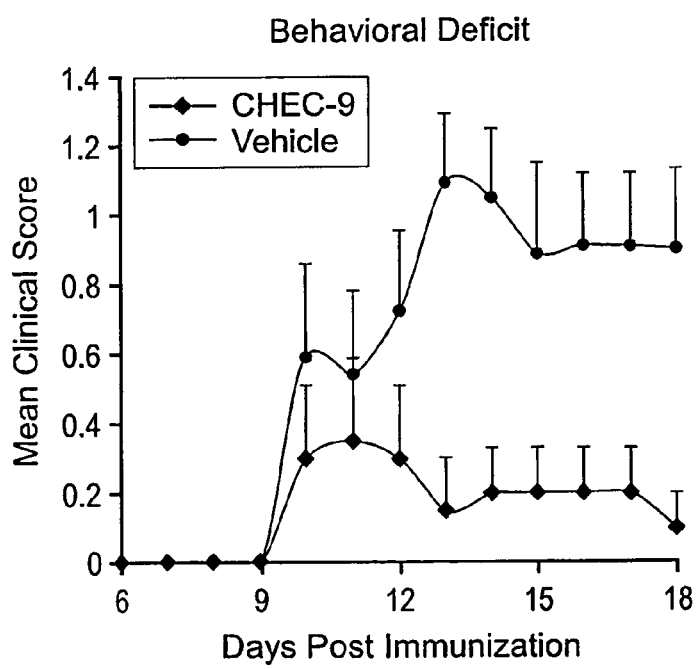
Figure 24:
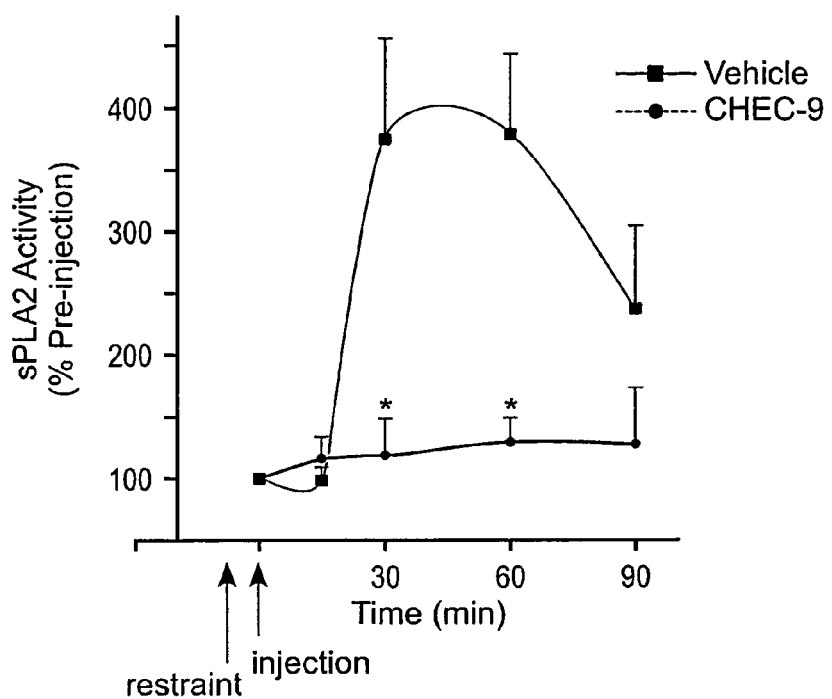
FIG. 24 is a graph depicting the attenuation of stress-induced sPLA2 enzyme in rat plasma samples after systemic delivery of CHEC-9. A transient rise in mean levels of active enzyme was found in the first 60 min after vehicle injections in rats subjected to immobilization stress. Subcutaneous CHEC-9 (0.4 mg/kg) inhibits this increase at 30 and 60 min. Each data point represents the mean±s.e.m. of the of 2-3 measurements from each of 4 rats in each of the two treatment groups. The values are expressed as a percent of the pre-injection samples for individual rats. (*) represents significant differences at 30 and 60 minutes (p<0.05 by Mann Whitney test).

There was an initial loss of body weight post-immunization (PI) in both CHEC-9 and vehicle treated rats. From post-immunization day 5 (the start of treatment) onward, peptide treated animals gained weight at a significantly higher rate than vehicle treated rats (0.517 g/day vs. 0.392 g/day, p=0.002 paired test of daily averages). Mean urinary PLA2 activity increased for the first 8 days PI in both groups of rats (FIG. 23A). CHEC-9 treatment resulted in a significant decline in activity between by days 8 and 10, just prior to the onset of the behavioral deficits (FIG. 23B). However, only 3/10 peptide-treated rats showed symptoms of disease and one of these had a late onset tail paresis (at day 17 post-immunization). This compares to 8/10 in the vehicle treated group showing generally more severe symptoms that appeared between days 10 and 13 PI. Nissl/myelin and Hemotoxylin and Eosin staining through the caudal-most spinal cord revealed pathology consistent with the clinical score. Large regions of densely packed small cells appeared in rats showing the most severe deficits (clinical score 2.0 or greater), presumably the result of perivascular effusion of peripheral immune cells).

PLA2 enzyme activity is increased in the urine of subjects with either active or stable MS, suggesting that these patients had increased levels of systemically active enzyme. It was somewhat surprising to find that PLA2 enzymes in urine react with substrate according to a typical hyperbolic function, but this result increases confidence that the measurements reflect levels of active enzyme. Furthermore, the same increase was found in rats following immunizations that produced EAE. Although the validity of EAE as a model for MS has been questioned, it is still useful in the present context to help define the role of PLA2 activity in the progress of autoimmune pathologies involving the nervous system. The attenuation of EAE by PLA2 inhibitor CHEC-9, along with similar results by others, also argues for a significant role for these enzymes in MS and related disorders. Interestingly, the effects of CHEC-9 were detected only at the peak of PLA2 activity, a few days after the start of treatment. Recent experiments suggest that CHEC-9 exhibits several properties of an uncompetitive inhibitor (i.e. it may bind the enzyme-substrate complex) when tested with purified sPLA2 group I and with human or rat plasma ex vivo. Therefore, the peptide may be effective with high enzyme-substrate availability, as would be expected during periods of excessive inflammation or oxidative stress, which could explain the delayed PLA2 response.

The therapeutic effects of CHEC-9 in EAE may be related to a decrease in PLA2-directed inflammation, or to a reduction in PLA2 potentiated excitoxicity. It is also possible that specific immunoregulatory functions of PLA2 enzymes are affected. Secreted PLA2s regulate T lymphocyte activity and levels of proinflammatory cytokines in a variety of cell types (either directly or via cytosolic PLA2), especially during periods of oxidative stress.

The results set forth herein suggest that further study of PLA2 regulated processes in EAE models may provide new insights into therapies for autoimmune disorders affecting the nervous system. Furthermore, monitoring PLA2 activity in MS patients, for example in relation to their susceptibility to relapse, could help define appropriate regimens for application of these new therapies.

The disclosure set forth herein also indicates that increased levels of sPLA2 enzymes, long associated with inflammation outside the nervous system, also characterize Multiple Sclerosis and Experimental Autoimmune Encephalomyelitis. Although the EAE model has been questioned recently in terms of its validity for identifying potential MS therapies, the model is clearly useful to help define the role of inflammatory enzymes, specifically the PLA2s, in autoimmune attack of the nervous system. Using a simple urinary assay for active enzyme concentration, it was demonstrated that rats immunized to produce EAE had increased systemic sPLA2 following immunization. The same assay applied to samples collected from MS patients also showed increased enzyme levels even with random or "spot" sampling. Based in part on the parallel results in the rodent model, it was concluded that sPLA2 inflammatory activity is ongoing in the majority of MS patients, active or stable, regardless of treatment. The highest levels of enzyme were found in patients with active disease, i.e., during relapse. Interestingly, asymptomatic EAE rats had elevated enzyme activity but became symptomatic only after the peak in measured activity, suggesting that elevated enzyme activity and behavioural deficits are correlated. Finally, and most important, EAE symptoms were attenuated by sPLA2 inhibitor CHEC-9. This finding supports the idea that PLA2 enzymes play a direct role in the pathogenesis of MS and related autoimmune disorders.

The kinetics of CHEC-9 inhibition of sPLA2 suggest that the peptide exhibits several properties of an uncompetitive inhibitor, which may help explain the delay between treatment and the ability to detect a reduction in enzyme activity. Since uncompetitive inhibitors depend on sufficient levels enzyme and substrate, it may be that those levels were not appropriate (at least for the present CHEC-9 dosage and treatment schedule) until sPLA2 activity was maximal, several days after the start of peptide treatment. In addition, it is under these conditions of inflammation and oxidative stress that sPLA2 may exert the most profound effects on the activity of cytosolic PLA2 (cPLA2). The specific involvement of cPLA2 in EAE has also been demonstrated. A straightforward explanation of the therapeutic effects of CHEC-9 is that peptide inhibition decreases sPLA2-mediated inflammation and the inflammatory products of PLA2 metabolism, either directly or via cross talk with cPLA2. Studies are in progress to test this proposition with reference to specific downstream products in PLA2 pathways. There are other properties of these enzymes that may be involved in regulating neuron viability and both innate and acquired immune responses. For example, sPLA2 enzymes potentiate excitotoxicity, a mechanism suggested to be involved in most instances of neurodegeneration. In addition, there are specific immunoregulatory functions of PLA2 enzymes that may be affected by this inhibitor. Secreted PLA2s regulate T lymphocyte activity and levels of proinflammatory cytokines in a variety of cell types (either directly or via cPLA2), especially during periods of oxidative stress. Thus, sPLA2 enzymes may be an important therapeutic target for a variety neurodegenerative disorders, particularly those with a strong inflammatory component.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

LITERATURE CITED

Abe K, Kogure K, Yamamoto H, Imazawa M, Miyamoto K. (1987) Mechanism of arachidonic acid liberation during ischemia in gerbil cerebral cortex. J Neurochem 48:503-509.

Abraham E, Naum C, Bandi V, Gervich D, Lowry S F, Wunderink R, Macias W, Skerjanee S, Dmitrienko A, Farid N, Forgue S T, Jiang F. (2003) Efficacy and safety of LY315920Na/S-5920, a selective inhibitor of 14-kDa group IIA secretory phospholipase A2, in patients with suspected sepsis and organ failure. Crit Care Med 31:718-728.

Abromson-Leeman S, Bronson R, Luo Y, Berman M, Leeman R, Leeman J, Dorf M. (2004) T-cell properties determine disease site, clinical presentation, and cellular pathology of experimental autoimmune encephalomyelitis. Am J Pathol 165:1519-1533.

Andreis P G, Buttazzi P, Tortorella C, DeCaro R, Aragona F, Neri G, Nussdorfer G G. (1999) The inhibitor of phospholipase-A2, AACOCF3, stimulates steroid secretion by dispersed human and rat adrenocortical cells. Life Sci 64:1287-1294.

Balboa M A, Perez R, Balsinde J. (2003) Amplification mechanisms of inflammation: Paracrine stimulation of arachidonic acid mobilization by secreted phospholipase $A_2$ is regulated by cytosolic phospholipase $A_2$-derived hydroperoxyeicosatetraenoic acid. J Immunol 989-994.

Balboa M A, Varela-Nieto I, Killermann Lucas K, Dennis E A. (2002) Expression and function of phospholipase A(2) in brain. FEBS Lett. 531(1):12-7.

Balsinde J, Dennis E A. (1996) Distinct roles in signal transduction for each of the phospholipase $A_2$ enzymes present in $P388D_1$ macrophages. J Biol Chem 271L6758.

Basu A, Krady J K, O'Malley M, Styren S D, DeKosky S T, Levison S W. (2002) The type 1 interleukin-1 receptor is essential for the efficient activation of microglia and the induction of multiple proinflammatory mediators in response to brain injury. J Neurosci 22:6071-6082.

Bazan N G, Colangelo V, Lukiw W J. (2002) Prostaglandins and other lipid mediators in Alzheimer's disease. Prostaglandins Other Lipid Mediat 68-69:197-201.

Beck S, Lambeau G, Scholz-Pedretti K, Gelb M H, Janssen M J W, Edwards S H, Wilton D C, Pfeilschifter J, Kaszkin M. (2003) Potentiation of tumor necrosis factor α-induced secreted phospholipase $A_2$ ($sPLA_2$)-IIA expression in mesangial cells by an autocrine loop involving $sPLA_2$ and peroxisome proliferator-activated receptor α activation. J Biol Chem 278:29799-29812.

Bohatschek M, Kloss C U A, Kalla R, Raivich G. (2001) In vitro model of microglial deramification: ramified microglia transform into amoeboid phagocytes following addition of brain cell membranes to microglia-astrocyte cocultures. J Neurosci Res 64:508-522.

Bolton C, Parker D, McLeod J, Turk, J L. (1986) A study of the prostaglandin and thromboxane content of the central nervous tissues with the development of chronic relapsing allergic encephalomyelitis. J Neuroimmunol 10:201-208.

Bolton C, Turner A M, Turk J L. (1984) Prostaglandin levels in cerebrospinal fluid from multiple sclerosis patients in remission and relapse. J Neuroimmunol 6:151-159.

Bradley J D, Dmitrienko A A, Kivitz A J, Gluck O S, Weaver A L, Wiesenhutter C, Myers S L, Sides G D. (2005) A randomized, double-blinded, placebo-controlled clinical trial of LY333013, a selective inhibitor of group II secretory phospholipae A2, in the treatment of rheumatoid arthritis. J Rheumatol 32:417-423.

Brusaferri F, Candelise L. (2000) Steroids for multiple sclerosis and optic neuritis: a meta-analysis of randomized controlled clinical trials. J Neurol 247:435-442.

Chakraborti S. (2003) Phospholipase $A_2$ isoforms: a perspective Cellular Signaling 15:637-665.

Couturier C, Brouillet A, Couriaud C, Koumanov K, Bereziat G, Andrean M. (1999) Interleukin 1beta induces type II-secreted phospholipase A(2) gene in vascular smooth muscle cells by a nuclear factor kappaB and peroxisome proliferator-activated receptor-mediated process. J Biol Chem 274:23085-23093.

Crowl R M, Stoller T J, Conroy R R, Stoner C R. (1991) Induction of phospholipase A2 gene expression in human hepatoma cells by mediators of the acute phase response. J Biol Chem 266:2647-2651.

Cummings B S, McHowat J, Schnellmann R G. (2000) Phospholipase $A_2S$ in cell injury and death. J Pharmacol & Exp Therap 294:793-799.

Cunningham, T. J. Souayah, N., Jameson, B., Mitchell, J. and Yao, L. 2004. Systemic treatment of cerebral cortex lesions in rats with a new phospholipase A2 inhibitor. J Neurotrauma, 21:1683-1691.

Cunningham T J, Jing H, Akerblom I, Morgan R, Fisher T S, Neveu M. (2002) Identification of the human cDNA for new survival/evasion peptide (DSEP): Studies in vitro and in vivo of overexpression by neural cells. Exp. Neurology, 177:32-39.

Cunningham, T. J., Jing H, Wang Y, Hodge L. (2000) Calreticulin binding and other biological activities of survival peptide Y-P30 including effects of systemic treatment of rats. Exp. Neurol. 163:457-468.

Cunningham, T J, Hodge 1, Speicher D, Reim D, Tyler-Polz C, Levitt P, Eagleson, K, Kennedy S, Wang Y (1998) Identification of a survival-promoting peptide in medium conditioned by oxidatively stressed cell lines of nervous system origin. J Neurosci 18:7047-7060.

DeCoster M A, Lambeau G, Lazdunski M, Bazan N G. (2002) Secreted phospholipase A2 potentiates glutamate-induced calcium increase and cell death of primary neuronal cultures. J Neurosci Res. 67:634-645.

Dore-Duffy P, Shih-Yieh H, Donovan C. (1991) Cerebrospinal fluid eicosanoid levels: endogenous PGD2 and LTC4 synthesis by antigen-presenting cells that migrate to the central nervous system. Neurol 41:322-334.

Eagleson K L, Cunningham T J, Haun F (1992) Rescue of both rapidly and slowly degenerating neurons in the dorsal lateral geniculate nucleus of adult rats by a cortically derived neuron survival factor. Exp Neurol 116:156-162.

Eagleson K L, Haun F, Cunningham T J (1990) Different populations of dorsal lateral geniculate nucleus neurons have concentration-specific requirements for a cortically derived neuron survival factor. Exp Neurol 110:284-290.

Farooqui A A, Litsky M L, Farooqui T, Horrocks L A. (1999) Inhibitors of intracellular phospholipase A2 activity: their neurochemical effects and therapeutical importance for neurological disorders. Brain Res Bull. 49:139-153.

Fasani F, Bocquet A, Robert P, Peterson A, Eyer J. (2004) The amount of neurofilaments aggregated in the cell body is controlled by their increased sensitivity to trypsin-like proteases. Science 117:861-869.

Fischer H G, Reichmann G. (2001) Brain dendritic cells and macrophages/microglia in central nervous system inflammation. J Immunol 166:2717-2726.

Flower R J, Blackwell G J. (1979) Anti-inflammatory steroids induce biosynthesis of a phospholipase A2 inhibitor which prevents prostaglandin generation. Nature 278:456-459.

Fonteh A N, Atsumi G, LaPorte T, Chilton F H. (2000) Secretory phospholipase $A_2$ receptor-mediated activation of cytosolic phospholipase $A_2$ in murine bone marrow-derived mast cells. J Immunol 165:2772-2782.

Fuentes L, Hernandez M, Nieto M L, Crespo, M S. (2002) Biological effects of group IIA secreted phospholipase $A_2$. FEBS Lett 531:7-11.

Gladue R P, Carroll L A, Milic A J, Scampoli D N, Stukenbrok H A, Pettipher E R, Salter E D, Contillo L, Showell H J. (1996) Inhibition of leukotriene B4-receptor interaction suppresses eosinophil infiltration and disease pathology in a murine model of experimental allergic encephalomyelitis. J Exp Med. 183:1893-1898.

Gordon T, Hegedus J, Tam S L. (2004) Adaptive and maladaptive motor axonal sprouting in aging and motoneuron disease. Neurol Res. 26:174-185.

Granata F, Petraroli A, Boilard E, Bezzine S. Bollinger J, DelVecchio L, Gelb M H, Lambeau G, Marone G, Triggiani M. (2005) Activation of cytokine production by secreted phospholipase A2 in human lung macrophages expressing the M-type receptor. J Immunol. 174:464-474.

Greco A, Minghetti L, Puopolo M, Cannoni S, Romano S, Pozzilli C, Levi G. (2004) Cerebrospinal fluid isoprostanes are not related to inflammatory activity in relapsing-remitting multiple sclerosis. J Neurol Sci 224:23-27.

Han W K, Sapirstein A, Hung C C, Alessandrini A, Bonventre J V. (2003) Cross-talk between cytosolic phospholipase A2 alpha (cPLA2alpha) and secretory phospholipase A2 (sPLA2) in hydrogen peroxide-induced arachidonic acid release in murine mesangial cells: sPLA2 regulates cPLA2 alpha activity that is responsible for arachidonic acid release. J Biol Chem. 278:24153-24163.

Hannon R, Croxtall J D, Getting S J, Roviezzo F, Yona S, Paul-Clark M J, Gavins F N, Perretti M, Morris J F, Buckingham J C, Flower R J. (2003) Aberrant inflammation and resistance to glucocorticoids in annexin 1-/- mouse. FASEB J. 17:253-255.

Haun F, Cunningham T J (1993) Recovery of frontal cortex-mediated visual behaviors following neurotrophic rescue of axotomized neurons in medial frontal cortex. J Neurosci 13(2):614-622.

Hendriks J J, Teunissen C E, de Vries H E, Dijkstra C D. (2005) Macrophages and neurodegeneration. Brain Res Rev 48:185-195.

Heppner F L, Greter M, Marino D, Falsig J, Raivich G, Hovelmeyer N, Waisman A, Rulicke T, Prinz M, Priller J, Becher B, Aguzzi A. (2005) Experimental autoimmune encephalomyelitis repressed by microglial paralysis. Nat. Med. 11: 146-152.

Hernandez M, Burillo S L, Crespo M S, Nieto M L. (1998) Secretory phospholipase A2 activates the cascade of mitogen-activated protein kinases and cytosolic phospholipase A2 in the human astrocytoma cell line 1321N1. J Biol Chem 273:606-612.

Hoozemans J J, Veerhuis R, Jansen I, Rozemuller A J, Eikelenboom P. (2001) Interleukin-1 beta induced cyclooxygenase 2 expression and prostaglandin E2 secretion by human neuroblastoma cells: implications for Alzheimer's disease. Exp Gerontol 36:559-570.

Kalyvas A, David S. (2004) Cytosolic phospholipase A2 plays a key role in the pathogenesis of multiple sclerosis-like disease. Neuron 41:323-335.

Kamiya S, Shirahase H, Nakamura S, Kanda M, Matsui H, Yoshimi A, Kasai M, Takahashi K, Kurahashi K. (2001) A novel series of thromboxane A2 synthetase inhibitors with free radical scavenging and anti-peroxidative activities. Chem Pharm Bull 49:563-571.

Kilvenyi P, Beal M F, Ferrante R J, Andreassen O A, Wermer M, Chin M R, Bonventre J V. (1998) Mice deficient in group IV cytosolic phospholipase A2 are resistant to MPTP neurotoxicity. J Neurochem 71:2634-2637.

Klegeris A, McGeer P L. (2003) Toxicity of human monocytic THP-1 cells and microglia toward SH-SY5Y neuroblastoma cells is reduced by inhibitors of 5-lipoxygenase and its activating protein FLAP. J Leukoc Biol 73:369-378.

Klegeris A, McGeer P L. (2000) Interaction of various intracellular signaling mechanisms involved in mononuclear phagocyte toxicity toward neuronal cells. J Leukoc Biol 67:127-133.

Kloss C U, Bohatschek M, Kreutzberg G W, Raivich G. (2001) Effect of lipopolysaccharide on the morphology and integrin immunoreactivity of ramified microglia in the mouse brain and in cell culture. Exp Neurol 168:32-46.

Kolko M, de Turco E B, Diemer N H, Bazan N G. (2002) Secretory phospholipase A2-mediated neuronal cell death involves glutamate ionotropic receptors. Neuroreport 13:1963-1966.

Kugiyama K, Ota Y, Sugiyama S, Kawano H, Doi H, Soejima H, Miyamoto S, Ogawa H, Takazoe K, Yasue H. (2000) Prognostic value of plasma levels of secretory type II phospholipase A2 in patients with unstable angina pectoris. Am J Cardiol. 86(7):718-22.

Kurtzke J F (1983) Rating neurologic impairment in multiple sclerosis: an expanded disability status scale (EDSS). Neurology; 33: 1444-1452.

Landgraf P, Sieg F, Wahl P, Meyers G, Kreutz M R, H-C Pape. (2004) A maternal blood-borne factor promotes survival of the developing thalamus, FASEB J. (in press).

Lehtonen J Y, Holopinen J M, Kinnunen P K. (1996) Activation of phospholipase A2 by amyloid beta-peptides in vitro. Biochem 35:9407-9414.

Lin M K, Farewell V, Vadas P, Bookman A A, Keystone E C, Pruzanski W. (1998) Secretory phospholipase A2 as an index of disease activity in rheumatoid arthritis. Inflammation 22:161-73.

Lipton P. Ischemic cell death in brain neurons. Physiol. Rev. 79:1431-1568, 1999.

Liu P-Y, Li Y-H, Tsai W-C, Chao T-H, Tsai L-M, Wu H-L, Chen J-H. (2003) Prognostic value and the changes of plasma levels of secretory type II phospholipase A2 in patients with coronary artery disease undergoing percutaneous coronary intervention. European Heart Journal 24: 1824-1832.

Lombardi V R, Garcia M, Cacabelos R. (1998) Microglial activation induced by factor(s) contained in sera from Alzheimer-related ApoE genotypes. J Neurosci Res 54:539-553.

Lukiw W J, Bazan N G. (2000) Neuroinflammatory signaling upregulation in Alzheimer's disease. Neurochem Res. 25:1173-1184.

Martino G, Adorini L, Rieckmann P, Hillert J, Kallmann B, Comi G, et al. (2002). Inflammation in multiple sclerosis: the good, the bad, and the complex. Lancet Neurol 1:499-509.

Miele L. (2003) New weapons against inflammation: dual inhibitors of phospholipase A2 and transglutaminase. J Clin Invest 111:19-21.

Mihelich E D, Carlson D G, Fox N, Song M, Schevitz R W, Snyder D W. (1997) Structure-based design and therapeutic potential of phospholipase A(2) inhibitors. Prog Surgery 24:140-145.

Millcevic I, Pekovic S, Subasic S, Mostarica-Stojkovic M, Stosic-Grujicic S, Medic-Mijacevic L, Pejanovic V, Rakic L, Stojiljkovic M. (2003) Ribavirin reduces clinical signs and pathological changes of experimental autoimmune encephalomyelitis in dark agouti rats. J Neurosci Res 72:268-278.

Milligan C E, Cunningham T J, Levitt P. (1991) Differential immunochemical markers reveal the normal distribution of brain macrophages and microglia in the developing rat brain. J Comp Neurol 314:125-135.

Moon C, Ahn M, Wie M B, Kim H M, Koh C S, Hong S C, Kim M D, Tanuma N, Matsumoto Y, Shin T. (2005) Phenidone, a dual inhibitor of cyclooxygenases and lipoxygenases, ameliorates rat paralysis in experimental autoimmune encephalomyelitis by suppressing its target enzymes. Brain Res. 1035:206-210.

Moon C, Ahn M, Jee Y, Heo S, Kim S, Kim H, Sim K B, Koh C S, Shin Y G, Shin T. (2004) Sodium-salicylate-induced amelioration of experimental autoimmune encephalomyelitis in Lewis rats is associated with the suppression of inducible nitric oxide synthase and cyclooxygenases. Neurosci Lett 356:123-126.

Mounier C M, Ghomashchi F, Lindsay M R, James S, Singer A G, Parton R G, Gelb M H. (2004) Arachidonic acid release from mammalian cells transfected with human groups IIA and X secreted phospholipase A(2) occurs predominantly during the secretory process and with the involvement of cytosolic phospholipase A(2)-alpha. J Biol Chem. 11; 279(24):25024-38.

Murakami M, Masuda S, Shimbara S, Bezzine S, Lazdunski M, Lambeau G, Gelb M H, Matsukura S, Kokubu F, Adachi M, Kudo I. (2003) Cellular arachidonate-releasing function of novel classes of secretory phospholipase $A_2S$ (Groups III and XII). J Biol Chem 278:10657-10667.

Neu I, Mallinger J, Wildfeuer A, Mehlber L. (1992) Leukotrienes in the cerebrospinal fluid of multiple sclerosis patients. Acta Neurol Scand 86:586-587.

Newman S P, Croxtall J D, Choudhury Q, Flower R J. (1997) The coordinate regulation of lipocortin 1, COX 2 and cPLA2 by IL-1 beta in A549 cells. Adv Exp Med Biol 407:249-253.

Pete M J, Wu D W, Exton J H. (1996) Subcellular fractions of bovine brain degrade phosphatidylcholine by sequential deacylation of the sn-1 and sn-2 positions. Biochim Biophys Acta 1299:325-332.

Peters-Golden M, Canetti C, Mancuso P, Coffey M J. (2005) Leukotrienes: underappreciated mediators of innate immune responses. J Immunol 174:589-594.

Petrovic N, Grove C, Langton P E, Misso N L, Thompson P J. (2001) A simple assay for a human serum phospholipase A2 that is associated with high-density lipoproteins. J Lipid Res 42:1706-13.

Phillis J W, O'Regan M H. (1996) Mechanisms of glutamate and aspartate release in the ischemic rat cerebral cortex. Brain Res 730:150-164.

Pinto F, Brenner T, Dan P, Krimsky M, Yedgar S. (2003) Extracellular phospholipase $A_2$ inhibitors suppress central nervous system inflammation. Glia 44:275-282.

Poligone B, Baldwin A S. (2001) Positive and negative regulation of NFkappaB by COX-2: roles of different prostaglandins. J Biol Chem 276:38658-38654.

Porter D, Weremowicz S, Chin K, Seth P, Keshaviah A, Lahti-Domenici J, Bae Y K, Monitto C L, Merlos-Suarez A, Chan J, Hulette C M, Richardson A, Morton C C, Marks (2003) A neural survival factor is a candidate oncogene in breast cancer. Proc Natl Acad Sci USA 100(19):10931-6.

Prat A, Antel J. (2005) Pathogenesis of multiple sclerosis. Curr Opin Neurol 18:255-230.

Raivich G, Banati R. (2004) Brain microglia and blood-derived macrophages: molecular profiles and functional roles in multiple sclerosis and animal models of autoimmune demyelinating disease. Brain Res Rev 46:261-281.

Rao M V, Nixon R A (2003) Defective neurofilament transport in mouse models of amyotrophic lateral sclerosis: a review. Neurochem Res. 28:1041-7.

Reder A T, Thapar M, Sapugay A M, Jensen M A. (1994) Prostaglandins and inhibitors of arachidonate metabolism suppress experimental allergic encephalomyelitis. J. Neuroimmunol 54:117-127.

Reder A T, Thapar M, Sapugay A M, Jensen M A. (1995) Eicosenoids modify experimental allergic encephalomyelitis. Am J Ther 2:711-720.

Rehncrona S, Westerberg E, Akesson B, Siesjo B K. (1982) Brain cortical fatty acids and phospholipids during and following complete and severe incomplete ischemia. J Neurochem 38:84-93.

Rothwell N J, Luheshi G N. (2000) Interleukin 1 in the brain: biology, pathology and therapeutic target. Trends Neurosci 23:618-625.

Saluja I, Song D, O'Regan M H, Philis J W. (1997) Role of phospholipase A2 in the release of free fatty acids during ischemia-reperfusion in rat cerebral cortex. Neurosci Lett 233:97-100.

Sapirstein A, Bonventre J V. (2000) Specific physiological roles of cytosolic phospholipase $A_2$ as defined by gene knockouts. Biochimica et Biophysica Acta 1488:139-148.

Schittek B, Hipfel R, Sauer B, Bauer J, Kalbacher H, Stevanovic S, Schirle M, Schroeder K, Blin N, Meier F, Rasner G, Garbe C. (2001) Dermcidin: a novel human antibiotic peptide secreted by sweat glands. Nat Immunol 2:1133-1137.

Sohn J, Kim T-I, Yoon Y-H, Kim J-Y, Kim S-Y. (2003) Novel transglutaminase inhibitors reverse the inflammation of allergic conjunctivitis. J Clin Invest 111:121-128.

Springer D M. (2001) An update on inhibitors of human 14 kDa Type II S-$PLA_2$ in development. Curr Pharmaceut Design 7:181-198.

Stefferl A, Storch M K, Linington C, Stadelmann C, Lassmann H, Pohl T, Holsboer F, Tilders F J, Reul J M. (2001). Disease progression in chronic relapsing experimental allergic encephalomyelitis is associated with reduced inflammation-driven production of corticosterone. Endocrinology 142:3616-3624.

Stosic-Grujicic S, Ramic Z, Bumbasirevic V, Harhaji L, Mostarica-Stojkovic M. (2004) Induction of experimental autoimmune encephalomyelitis in dark agouti rats without adjuvant. Clin Exp Immunol 136:49-55.

Stys P K, Jiang Q. (2002) Calpain-dependent neurofilament breakdown in anoxic and ischemic rat central axons. Neurosci Lett 328:150-154.

Taketo M M, Sonoshita M. (2002) Phospholipase $A_2$ and apoptosis. Biochim et Biophysica Acta 1585:72-76.

Thommesen L, Sjursen W, Gasvik K, Hanssen W, Brekke O L, Skattebol L, Holmeide A K, Espevik T, Johansen B, Laegreid A. (1998) Selective inhibitors of cytosolic or secretory phospholipase A2 block TNF-induced activation of transcription factor nuclear factor-kappa B and expression of ICAM-1. J Immunol 161:3421-3430.

Tilley S L, Coffman T M, Koller B H. (2001). Mixed messages: modulation of inflammation and immune responses by prostaglandins and thromboxanes. J Clin Invest 108:15-23.

Todorov P, Cariuk P, McDevitt T, Coles B, Fearon K, Tisdale M. (1996) Characterization of a cancer cachectic factor. Nature 379:739-42.

Triggiani M, Granata F, Balestrieri B, Petraroli A, Scalia G, Del Vecchio L, Marone G. (2003) Secretory phospholipases $A_2$ activate selective functions in human eosinophils. J Immunol 170:3279-3288.

Valentin E, Lambeau G. (2000) Increasing molecular diversity of secreted phospholipases A(2) and their receptors and binding proteins. Biochim Biophys Acta 1488:59-70.

Vishwanath B S, Frey F J, Bradbury M J, Dallman M F, Frey B M. (1993) Glucocorticoid deficiency increases phospholipase A2 activity in rats. J Clin Invest 92:1974-1980.

Yagami T, Ueda K, Asakura K, Sakaeda T, Hata S, Kuroda T, Sakaguchi G, Itoh N, Hashimoto, Y, Hori Y. (2003) Porcine pancreatic group IB secretory phospholipase A2 potentiates Ca2+ influx through L-type voltage-sensitive Ca2+ channels. Br Res 960:71-80.

Yagami T, Ueda K, Asakura K, Hata S, Kuroda T, Sakaeda T, Takasu N, Tanaka K, Gemba T, Hori Y. (2002a) Human group IIA secretory phospholipase A2 induces neuronal cell by apoptosis. Mol Pharmacol 61:114-126.

Yagami T, Ueda K, Asakura K, Hata S, Kuroda T, Sakaeda T, Kishino J, Sakaguchi G, Itoh N, Hori Y. (2002b) Group IB secretory phospholipase A(2) induces cell death in the cultured cortical neurons possible involvement of its binding sites. Brain Res. 949:197-201.

Yoshida S, Ikeda M, Busto R, Santiso M, Martinez E, Ginsberg M D. (1986) Cerebral phosphoinositide, triacylglycerol and energy metabolism in reversible ischemia: origin and fate of free fatty acids. J Neurochem 47:744-757.

Yoshizawa N, Oshima S, Sagel I, Shimizu J, Treser G (1992) Role of a streptococcal antigen in the pathogenesis of acute poststreptococcal glomerulonephritis. Characterization of the antigen and a proposed mechanism for the disease. J Immunol 148:3110-63116.

Young W, Spinal cord contusion models. Prog Brain Res. 2002; 137:231-55.

What is claimed is:

1. A method of treating a mammal afflicted with an inflammatory condition, said method comprising administering a therapeutically effective amount of a polypeptide consisting of nine (9) amino acids consisting of the sequence of CHEASAAQC (SEQ ID NO:1) to said mammal, wherein said polypeptide inhibits the activity of phospholipase A2 (PLA2).

2. The method of claim 1, wherein said polypeptide is administered by at least one route selected from the group consisting of parenterally, orally, intramuscularly, and systemically.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys His Glu Ala Ser Ala Ala Gln Cys
1               5
```